United States Patent
Lee

(10) Patent No.: US 10,017,566 B2
(45) Date of Patent: Jul. 10, 2018

(54) GROWTH DIFFERENTIATION FACTOR (GDF) FOR TREATMENT OF DIASTOLIC HEART FAILURE

(71) Applicant: THE BRIGHAM AND WOMEN'S HOSPITAL, INC., Boston, MA (US)

(72) Inventor: Richard Theodore Lee, Weston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 15/032,089

(22) PCT Filed: Nov. 11, 2014

(86) PCT No.: PCT/US2014/064922
§ 371 (c)(1),
(2) Date: Apr. 26, 2016

(87) PCT Pub. No.: WO2015/073396
PCT Pub. Date: May 21, 2015

(65) Prior Publication Data
US 2016/0264657 A1  Sep. 15, 2016

Related U.S. Application Data

(60) Provisional application No. 61/902,928, filed on Nov. 12, 2013.

(51) Int. Cl.
*C12N 15/113* (2010.01)
*C07K 16/22* (2006.01)
*C07K 14/47* (2006.01)
*C07K 14/51* (2006.01)

(52) U.S. Cl.
CPC .......... *C07K 16/22* (2013.01); *C07K 14/4703* (2013.01); *C07K 14/51* (2013.01); *C07K 2317/24* (2013.01); *C07K 2317/34* (2013.01)

(58) Field of Classification Search
CPC .................................................. C12N 15/113
See application file for complete search history.

(56) References Cited

U.S. PATENT DOCUMENTS

| | | | |
|---|---|---|---|
| 6,008,434 | A | 12/1999 | Lee et al. |
| 6,517,835 | B2 | 2/2003 | Lee et al. |
| 2006/0078532 | A1 | 4/2006 | Omoigui |
| 2007/0253962 | A1* | 11/2007 | Hirsch ................ A61K 38/177 424/145.1 |
| 2007/0275895 | A1* | 11/2007 | Duan ................ C07K 14/4703 514/9.8 |
| 2008/0044387 | A1* | 2/2008 | Conboy ................ A61K 35/34 424/93.3 |
| 2008/0051328 | A1 | 2/2008 | Sharma et al. |
| 2009/0298761 | A1 | 12/2009 | Engelman |

FOREIGN PATENT DOCUMENTS

| | | |
|---|---|---|
| JP | 09501304 A | 2/1997 |
| WO | 1994/026892 A1 | 11/1994 |
| WO | 98/35019 A1 | 8/1998 |
| WO | 98/54572 A1 | 12/1998 |
| WO | 1999/037320 A1 | 7/1999 |
| WO | 2004/073633 A2 | 9/2004 |
| WO | 2008/109167 A2 | 9/2008 |
| WO | 2013/142114 A1 | 9/2013 |
| WO | WO-2016049662 A1 * | 3/2016 ............. C07K 16/22 |

OTHER PUBLICATIONS

Tsuchida et al. (Cell Commun. Signal 7:15 (Year: 2009).*
Wu Neuron 37:197-208 (Year: 2003).*
Brun et al. Cell Metabolism 22:54-56 (Year: 2015).*
Ahn et al., "Evaluation of growth differentiation factor 11 (GDF11) levels in dogs with chronic mitral valve insufficiency", The Canadian Journal of Veterinary Research 80(1): 90-92 (2016).
Breitbart, "Myostatin from the heart: local and systemic actions in cardiac failure and muscle wasting", Am J Physiol Heart Circ Physiol. 300(6):H1973-H1982 (2011).
Conboy et al., "Heterochronic parabiosis for the study of the effects of aging on stem cells and their niches", Cell Cycle 11(12):2260-2267 (2012).
Dai et al., "Overexpression of Catalase Targeted to Mitochondria Attenuates Murine Cardiac Aging", Circulation 119 (21):2789-2797 (2009).
Gamer et al., "Gdf11 is a Negative Regulator of Chondrogenesis and Myogenesis in the Developing Chick Limb", Developmental Biology 229(2):407-420 (2001).
Harmon et al., "GDF11 modulates NGN3+ islet progenitor cell number and promotes β-cell differentiation in pancreas development", Development 131(24):6163-6174 (2004).
Lee et al., "Regulation of GDR-11 and myostatin activity by GASP-1 and GASP-2", PNAS 110(39):E3713-E3722 (2013).
Li et al., "Transgenic overexpression of bone morphogenetic protein 11 propeptide in skeleton enhances bone formation", Biochemical and Biophysical Research Communications 416(3):289-292 (2011).
Lima et al., "Myostatin and follistatin expression in skeletal muscles of rats with chronic heart failure", Int J Exp Path. 51(1):54-62 (2010).
Loffredo et al., "Growth Differentiation Factor 11 is a Circulating Factor that Reverses Age-Related Cardiac Hypertrophy", Cell 153(4):828-839 (2013).
McNally "Questions and Answers About Myostatin, GDF11, and the Aging Heart", Circ Res. 118(1):6-8 (2016).
McPherron et al., "Redundancy of myostatin and growth/differentiation factor I I function", BMC Developmental Biology 9:1-9 (2009).
Morissette et al., "Myostatin Regulates Cardiomyocyte Growth Through Modulation of AKT Signaling", Circ Res. 39(1):15-24 (2006).
Ngo et al., "Computational Complexity, Protein Structure Prediction, and the Levinthal Paradox", The Protein Folding Jroblem and Tertiary Structure Prediction, Birkhauser Boston 492-495 (1994).

(Continued)

*Primary Examiner* — Brian A Whiteman
(74) *Attorney, Agent, or Firm* — Nixon Peabody LLP; David S. Resnick; Nicole D. Kling

(57) ABSTRACT

The methods and uses described herein relate to the treatment of age-related conditions, e.g. by administering an agent that inhibits the interaction of GDF11 and follistatin. In some embodiments, the agent can bind to an epitope of GDF11 as described herein.

8 Claims, 16 Drawing Sheets

(56) References Cited

OTHER PUBLICATIONS

Phillips, "The challenge of gene therapy and DNA delivery", Journal of Pharmacy and Pharmacology 53 (9):1169-1174 (2001).
Poggioli et al., "Circulating Growth Differentiation Factor 11/8 Levels Decline With Age", Circ Res. 118(1):29-37 (2016).
Shyu et al., "Myostatin expression in ventricular myocardium in a rat model of volume-overload heart failure", European Journal of Clinical Investigation 36:713-719 (2006).
Smith et al., "GDF11 Does Not Rescue Aging-Related Pathological Hypertrophy", Circ Res. 117(11):926-932 (2015).
Souza et al., "Proteomic Identification and Function Validation of Activins and Bone Morphogenetic Protein 11 as candidate Novel Muscle Mass Regulators", Molecular Endocrinology 22(12):2689-2702 (2008).
Tokuriki et al., "Stability effects of mutations and protein evolvability", Current Opinion in Structural Biology 19 (5):596-604 (2009).
Vidal et al., "Making sense of antisense", European Journal of Cancer 41(18):2812-2818 (2005).
Wells, "Additivity of Mutational Effects in Proteins", Biochemistry 29(37):8509-8517 (1990).
Zhou et al., "Reversal of Cancer Cachexia and Muscle Wasting by ActRIIB Antagonism Leads to Prolonged Survival", Cell 142:531-543 (2010).
Olson et al., "Association of growth differentitation fact 11/8, putative anti-ageing factro, with cardiovascular outcomes and overall mortality in humans: analysis of the Heart and Soul and HUNT3 cohorts", European Heart Journal 36(48):3426-3434 (2015).

\* cited by examiner

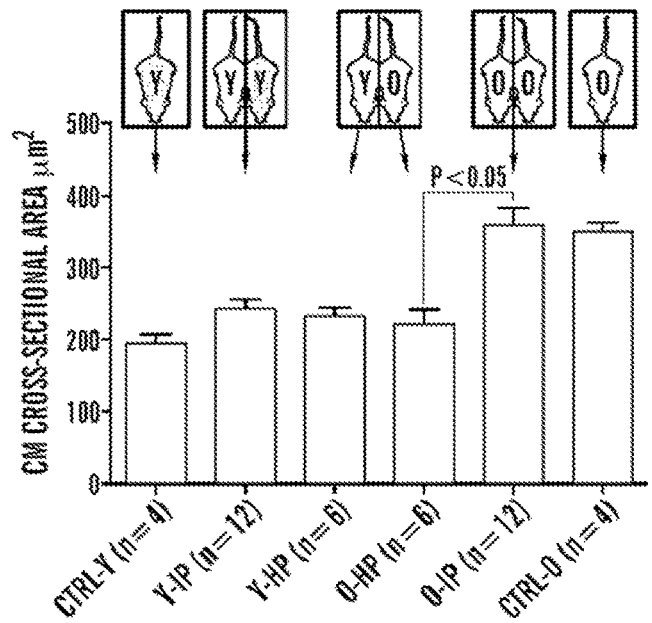
FIG. 2A
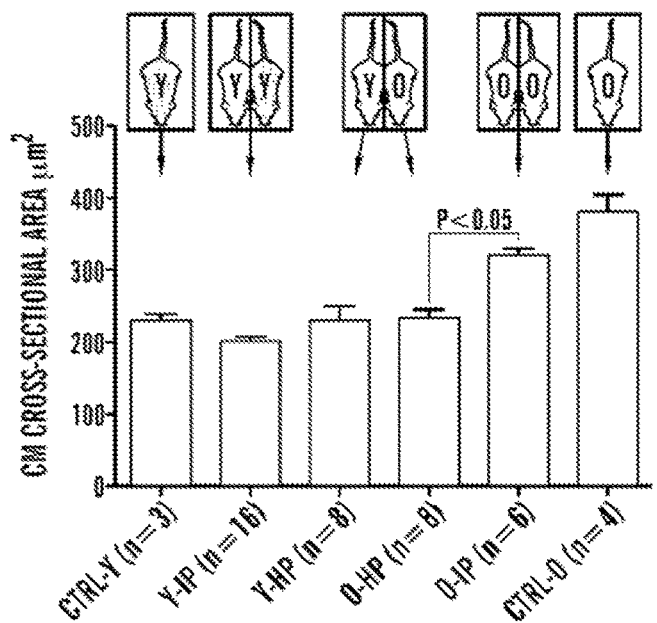
FIG. 2B
Figs. 2A-2B

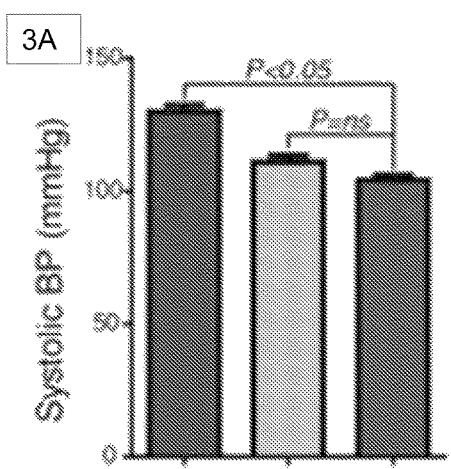
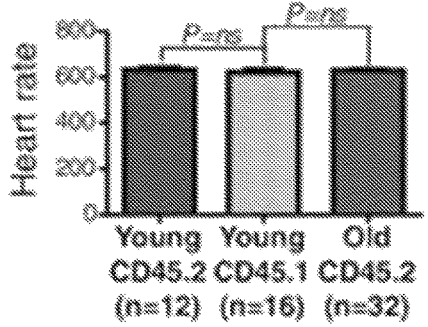
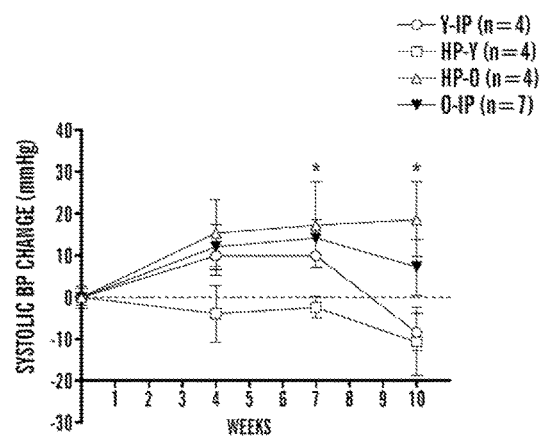
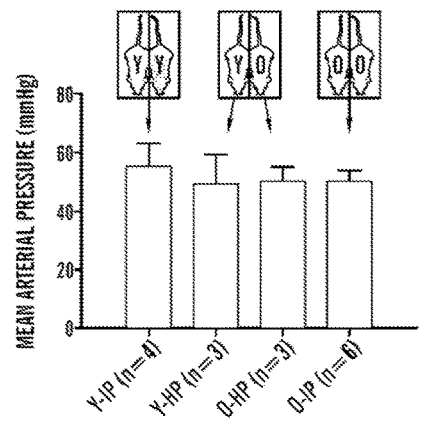
Figs. 3A-3C

```
>lcl|8305 unnamed protein product
Length=375

Score =  492 bits (1266),  Expect = 3e-177, Method: Compositional matrix adjust.
 Identities = 227/347 (65%), Positives = 279/347 (80%), Gaps = 11/347 (3%)

Query  62   CPVCVWRQHSPELRLESIKSQILSKLRLKEAPNISREVVKQLLPKAPPLQQILDLHDFQG   121
            C C W+Q+++  R+E+IK QILSKLRL+ APNIS++V++QLLPKAPPL++++D +D Q
Sbjct  39   CNACTWRQNTKSSRIEAIKIQILSKLRLETAPNISKDVIRQLLPKAPPLPELIDQYDVQR   98

Query  122  DALQPEDFLEEDEYHATTETVISHAQETDPAVQTDGSPLCCHFHFSPKVHFTKVLKAQLW   181
            D   +  LE+D+YHATTET+I+H  E+D  +Q DG P CC F FS K+ + KV+KAQLW
Sbjct  99   DD-SSDGSLEDDDYHATTETIITHPTESDFLMQYDGKPKCCFFKFSSKIQTMKVVKAQLW   157

Query  182  VYLRPVPRPATVYLQILRL-KPLTGEGTAGGGGGGRRHIRIRSLKIELHSRSGHWQSIDF   240
            +YLRPV P TV++QILRL KP+           G R+  IRSLK++++  +G WQSID
Sbjct  158  IYLRPVETPTTVFVQILRLIKPMKD----------GTRYTGIRSLKLDMNPGTGIWQSIDV   208

Query  241  KQVLHSWFRQPQSNWGIEINAFDPSGTDLAVTSLGPGAEGLHPFMELRVLENTKRSRRNL   300
            K VL +W +QP+SN GIEI A D +G DLAVT  GPG +GL+PF+E++V +  KPSRR+
Sbjct  209  KTVLQNWLKQPESNLGIEIKALDENGHDLAVTFPGPGEDGLNPFLEVRVTDTPKRSPRDF   268

Query  301  GLDCDEHSSESRCCRYPLTVDFEAFGWDWIIAPKRYKANYCSGQCEYMFMQKYPHTHLVQ   360
            GLDCDEHS+ESRCCRYPLTVDFEAFGWDWIIAPKRYKANYCSG+CE++F+QKYPHTHLV
Sbjct  269  GLDCDEHSTESRCCRYPLTVDFEAFGWDWIIAPKRYKANYCSGECEFVFLQKYPHTHLVH   328

Query  361  QANPRGSAGPCCTPTKMSPINMLYFNDKQQIIYGKIPGMVVDRCGCS   407
            QANPRGSAGPCCTPTKMSPINMLYFN K+QIIYGKIP MVVDRCGCS
Sbjct  329  QANPRGSAGPCCTPTKMSPINMLYFNGKEQIIYGKIPAMVVDRCGCS   375
```

Fig. 8

```
>lcl|1497 unnamed protein product
Length=405

Score =  727 bits (1876),  Expect = 0.0, Method: Compositional matrix adjust.
 Identities = 359/361 (99%), Positives = 359/361 (99%), Gaps = 0/361 (0%)

Query  47   RSSRPAPSVAPEPDGCPVCWRQHSRELRLESIKSQILSKLRLKEAPNISPEVVKQLLPK   106
            RSSRPAPS  PEPDGCPVCWRQHSRELRLESIKSQILSKLRLKEAPNISPEVVKQLLPK
Sbjct  45   RSSRPAPSAPPEPDGCPVCWRQHSRELRLESIKSQILSKLRLKEAPNISPEVVKQLLPK   104

Query  107  APPLQQILDLHDFQGDALQPEDFLEEDEYHATTETVISHAQETDPAVQTDGSPLCCHFHF   166
            APPLQQILDLHDFQGDALQPEDFLEEDEYHATTETVISHAQETDPAVQTDGSPLCCHFHF
Sbjct  105  APPLQQILDLHDFQGDALQPEDFLEEDEYHATTETVISHAQETDPAVQTDGSPLCCHFHF   164

Query  167  SPKVHFTKVLKAQLWVYLRPVFRPATVYLQILRLKPLTGEGTAGGGGGGRRHIRIRSLKI   226
            SPKVHFTKVLKAQLWVYLRPVFRPATVYLQILRLKPLTGEGTAGGGGGGRRHIRIRSLKI
Sbjct  165  SPKVHFTKVLKAQLWVYLRPVFRPATVYLQILRLKPLTGEGTAGGGGGGRRHIRIRSLKI   224

Query  227  ELHSRSGHWQSIDFKQVLHSWFRQPQSNWGIEINAFDPSGTDLAVTSLGPGAEGLHPFME   286
            ELHSRSGHWQSIDFKQVLHSWFRQPQSNWGIEINAFDPSGTDLAVTSLGPGAEGLHPFME
Sbjct  225  ELHSRSGHWQSIDFKQVLHSWFRQPQSNWGIEINAFDPSGTDLAVTSLGPGAEGLHPFME   284

Query  287  LRVLENTKPSRRNLGLDCDEHSSESRCCRYPLTVDFEAFGWDWIIAPKPYKANYCSGQCE   346
            LRVLENTKPSRRNLGLDCDEHSSESRCCRYPLTVDFEAFGWDWIIAPKPYKANYCSGQCE
Sbjct  285  LRVLENTKPSRRNLGLDCDEHSSESRCCRYPLTVDFEAFGWDWIIAPKPYKANYCSGQCE   344

Query  347  YMFMQKYPHTHLVQQANPRGSAGPCCTPTKMSPINMLYFNDKQQIIYGKIPGMVVDRCGC   406
            YMFMQKYPHTHLVQQANPRGSAGPCCTPTKMSPINMLYFNDKQQIIYGKIPGMVVDRCGC
Sbjct  345  YMFMQKYPHTHLVQQANPRGSAGPCCTPTKMSPINMLYFNDKQQIIYGKIPGMVVDRCGC   404

Query  407  S   407
            S
Sbjct  405  S   405
```

Fig. 9

GROWTH DIFFERENTIATION FACTOR (GDF) FOR TREATMENT OF DIASTOLIC HEART FAILURE

CROSS-REFERENCE TO RELATED APPLICATIONS

This application is a 35 U.S.C. § 371 National Phase Entry Application of International Application No. PCT/US2014/064922 filed Nov. 11, 2014, which designates the U.S. and claims benefit under 35 U.S.C. § 119(e) of U.S. Provisional Application No. 61/902,928 filed Nov. 12, 2013, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 10, 2014, is named 043214-079691-PCT_SL.txt and is 29,682 bytes in size.

TECHNOLOGICAL FIELD

Embodiments of the technology described herein relate to treatments for diastolic heart failure, cardiac hypertrophy, and related conditions.

BACKGROUND

Aging of multicellular organisms can lead to the loss of normal cardiac function, ultimately resulting in heart failure. Heart failure affects approximately 1% of individuals over 50 but over 5% of individuals over 75, and with the ongoing steep rise in the proportion of elderly individuals within our population, age-related heart failure is certain to become an increasingly prevalent health condition. Most age-related heart failure is in the setting of normal systolic function, and this is a condition often associated with cardiac hypertrophy (i.e. enlargement of heart tissue) and called "diastolic heart failure" (G, P. Aurigemma, N Engl J Med 355, 308 (Jul. 20, 2006)). Diastolic heart failure accounts for 40-60% of heart failure cases (G, P. Aurigemma, N Engl J Med 2006 355: 308; S. A. Hunt et al., Circulation 2009 119:e391; D. W. Kitzman, K. R. Daniel, Clin Geriatr Itled 2007 23:83; J. C. Finerty, Physiol Rev 1952 32:277). The prognosis of diastolic heart failure may be as poor as systolic heart failure (G, P. Aurigemma, N Engl J Med 2006 355:308), with a 5-year risk of death after an initial heart failure hospitalization approaching that of common malignancies (D. E. Wright, et al. Science 2001 294:1933). Although much progress has been made in the treatment of systolic heart failure, with substantial improvements in outcome over the past two decades, progress in treatment of diastolic heart failure has been much more elusive (S. A. Hunt et al., Circulation 119, e391 (Apr. 14, 2009)). Indeed, one can argue that there are no specific therapies for patients who experience the ventricular "stiffening" associated with the diastolic dysfunction that accompanies aging (D. W. Kitzman, K. R. Daniel, Clin Geriatr Itled 23, 83 (February, 2007)). It is this clinical reality that may explain the observation that mortality is declining for systolic heart failure but not diastolic heart failure (J. C. Finerty, Physiol Rev 1952 32:277), and underscores the enormous clinical demand for new therapeutic strategies targeting diastolic failure.

Diastolic heart failure is a clinical syndrome that occurs in a variety of pathophysiologic settings, including long-standing hypertension, valvular disease such as aortic stenosis, genetic hypertrophic cardiomyopathy, and as a result of aging. These disparate etiologies converge with some common pathophysiologic threads, most obviously with cellular hypertrophy or increased diameter of cardiomyocytes; which translates into increased thickness of the heart wall without significantly reducing squeezing capacity (systolic function). Myocardial hypertrophy is an important contributor to the impairment in relaxation or increased stiffness that causes diastolic heart failure (A. J. Wagers, et al., Science 2002 297:2256).

SUMMARY

Embodiments of the technology described herein are based on the discovery that the level of GDF11 in the blood of an animal decreases with age and this decrease in GDF11 level is associated with cardiac hypertrophy in the aging animal. The inventors have further discovered the therapeutic potential of increasing the GDF11 level in an animal, particularly as it relates to cardiac conditions, including those associated with aging. Additionally, the inventors have found that inhibiting the interaction of GDF11 and one or more follistatins (e.g. FSTL3) can increase the level of free GDF11 in circulation. Accordingly, provided herein are methods related to Follistatin-GDF11 inhibitors, e.g. compositions which inhibit the interaction of a GDF11 polypeptide and a follistatin polypeptide.

In one aspect, described herein is a method of treating an age-related condition, the method comprising administering to a subject a follistatin-GDF11 inhibitor. In some embodiments, the age-related condition is selected from the group consisting of a cardiovascular condition; aging of the heart; aging of skeletal muscle; aging of the brain; a metabolic disorder; and obesity. In one aspect, described herein is the use of a follistatin-GDF11 inhibitor for the treatment of a condition selected from the group consisting of a cardiovascular condition; aging of the heart; aging of skeletal muscle; aging of the brain; diastolic heart failure; cardiac hypertrophy; age-related cardiac hypertrophy; hypertension; valvular disease; aortic stenosis; genetic hypertrophic cardiomyopathy; stiffness of the heart due to aging; obesity; and a metabolic disorder.

In some embodiments, the subject has or has been diagnosed with a condition selected from the group consisting of diastolic heart failure; cardiac hypertrophy; age-related cardiac hypertrophy; hypertension; valvular disease; aortic stenosis; genetic hypertrophic cardiomyopathy; or stiffness of the heart due to aging. In some embodiments, the level of GDF11 polypeptide in the subject is increased. In some embodiments, the level of GDF11 polypeptide is the level of free GDF11. In some embodiments, the level of GDF11 polypeptide is the level of GDF11 in the circulation of the subject. In some embodiments, the level of GDF11 polypeptide is the level of GDF11 in the cardiac tissue of the subject. In some embodiments, the follistatin-GDF11 inhibitor comprises an inhibitory nucleic acid; an antibody reagent; an antibody; or a small molecule. In some embodiments, comprises an antibody reagent that binds specifically to an epitope comprised by SEQ ID NO: 15 or SEQ ID NO: 16. In some embodiments, the antibody reagent is selected from the group consisting of a humanized antibody reagent; a monoclonal antibody; and a humanized monoclonal antibody. In some embodiments, the composition is administered via a route selected from the group consisting of intravenously; subcutaneously; intra-arterial; and intra-coronary arterial. In some embodiments, the level of GDF11 is increased by at least 100%. In some embodiments, the level of GDF11 is increased to at least 75% of a healthy reference level.

In one aspect, described herein is a pharmaceutical composition comprising an isolated follistatin-GDF11 inhibitor and a pharmaceutically acceptable carrier.

BRIEF DESCRIPTION OF THE DRAWINGS

FIG. 1A depicts a schematic of the experiment. Six pairs of young isochronic, heterochronic and old isochronic parabiotic mice were generated. Four weeks after surgery mice were sacrificed and tissues harvested for analysis. FIG. 1B demonstrates a dramatic reduction in heart size in old mice exposed to a young circulation for 4 weeks. In heterochronic parabionts, the hypertrophy of the older heart appears to regress, while the younger parabiont heart does not develop hypertrophy. FIG. 1C depicts a graph representing the heart weight:tibia length ratio after 4 weeks of parabiosis, Data shown as mean±s.e.m.

FIGS. 2A-2B demonstrate reversal of age-related cardiomyocyte hypertrophy by exposure to a young circulation. FIG. 2A depicts myocyte cross-sectional area in LV based on PAS staining in females. For each animal, myocyte size was determined from cross-sectional area measurements of 100-200 myocytes in 5 independent myocardial sections. Results are based on the average from 4 to 12 animals per group. FIG. 2B depicts the results when the experiment was performed using male mice. Data shown as mean±s.e.m.

FIGS. 3A-3C demonstrate that the reversal of cardiac hypertrophy in old mice exposed to a young circulation is not explained by a reduction in blood pressure in old heterochronic parabiotic mice. FIG. 3A depicts measurements of blood pressure and pulse. Systolic blood pressure was measured on unoperated young and old mice at baseline using a computerized tail-cuff system. Pulse rate was measured using the same system. Young (2 months) mice show a significantly higher systolic blood pressure when compared to old (21 months) mice with no difference in pulse rate. FIG. 2B depicts the results when using a tail-cuff system modified to hold parabiotic pairs to measure blood pressure simultaneously at 4, 7 and 10 weeks after mice were conjoined. Old heterochronic mice showed a significant increase in systolic blood pressure at 7 and 10 weeks; old isochronic mice had a significant increase in blood pressure at 7 weeks when compared to baseline values, *: P<0.05. FIG. 3C depicts the values obtained for mean arterial pressure when determined by performing terminal intra-arterial catheterizations obtained simultaneously on paired mice after they had been conjoined for 10 wks. No significant differences were observed between the different groups. Data shown as mean±s.e.m.

FIG. 4C depicts a graph demonstrating that SERCA-2 transcript levels were significantly higher in old mice exposed to a young circulation when compared to old isochronic mice. Transcript levels measured with real-time PCR and normalized to the Y-IP group. Data shown as mean±s.e.m.

FIG. 6A presents a schematic of the experiment, wherein young isochronic, heterochronic, and old isochronic parabiotic mice were generated. Ten weeks after surgery mice were sacrificed and tissues harvested for analysis. FIG. 6B depicts a graph representing the heart weight:tibia length ratio after 10 weeks of parabiosis, Data shown as mean±SEM FIGS. 7A-7B demonstrate that young mice have a higher level of GDF11 than older mice.

FIG. 7A depicts the results of an ELISA assay while

FIG. 8 depicts an alignment of human GDF11 precursor polypeptide (query sequence; residues 62-407 of SEQ ID NO: 1) and human GDF8 precursor polypeptide (subject sequence; SEQ ID NO: 12).

FIG. 9 depicts an alignment of human GDF11 precursor peptide (query sequence; residues 47-407 of SEQ ID NO:1) and murine GDF11 precursor peptide (subject sequence; SEQ ID NO: 17).

FIG. 10A depicts a graph representing the heart weight/tibia length ratio after 4 weeks of parabiosis, using only CD45.2 mice.

FIG. 10B depicts a graph of left ventricular myocyte cross-sectional area based on PAS staining in CD45.2 mice. Exposure of an old mouse to the circulation of a young CD45.2 mouse reverses cardiac hypertrophy. FIG. 10C depicts a graph demonstrating that old mice conjoined to young CD45.1 or CD45.2 mice show no difference in blood pressure measured by the tail-cuff system after 4 weeks. FIG. 10D depicts a graph demonstrating that no significant intergroup differences in blood pressure were detected with terminal intra-arterial catheter-based measurements. Data shown as mean±s.e.m.

FIG. 11A depicts flow cytometry plots depicting CD45.1 (y-axis) or CD45.2 expression (x-axis) by splenocytes isolated from young or old mice joined by sham heterochronic parabiosis. Sham parabiotic pairs showed no cross-circulation of partner-derived blood cells as is observed in experimental parabiosis. FIG. 11B depicts a graph representing the heart weight/tibia length ratio after 4 weeks of sham parabiosis. FIG. 11C depicts a graph of left ventricular myocyte cross-sectional area based on PAS staining after 4 weeks of sham parabiosis. Data shown as mean±s.e.m.

FIG. 12A depicts the results of Western Blot analysis demonstrating reduced levels of GDF11 in the plasma of old mice compared to young mice (n=3 per group) Similarly GDF11 is reduced in the plasma of old isochronic (O-IP) compared to young isochronic (Y-IP) mice and is restored to "youthful" levels in old mice after exposure to a young circulation (O-HP) (n=3 per group). FIG. 12B depicts a graph of phenylephrine-induced cardiac hypertrophy measured by $^3$H-leucine incorporation in cardiac myocytes exposed to rGDF11 or myostatin. rGDF11 (50 nM) prevented phenylephrine-induced $^3$H-leucine incorporation. FIG. 12C demonstrates that GDF11 signals through a TGFβ pathway and suppresses Forkhead transcription factor phosphorylation in human cardiomyocytes. Western blots of human induced pluripotent stem cell-derived cardiomyocytes stimulated for 15 min with serum free media (Control) or with the same media containing the indicated proteins. FIG. 12D depicts a graph of randomized, vehicle controlled study of rGDF11 therapy in aged (23 mos) mice. rGDF11 (0.1 mg/kg) or saline (vehicle control) administered by daily intraperitoneal injection for 30 d. Graph representing heart weight/tibia length ratio. FIG. 12E depicts a graph of left ventricular myocyte cross-sectional area measured after PAS staining. rGDF11 therapy leads to a reduction in myocyte cross sectional area. FIG. 12F depicts graphs of expression of ANP, BNP or SERCA-2 in hearts harvested from old mice treated with rGDF11 or saline. Real-time PCR transcript measurements are normalized to levels in the saline group. Data shown as mean±s.e.m.

FIG. 13A depicts a graph of expression of GDF11 in tissues harvested from young (3 months old) mice. Real-time PCR transcript measurements are normalized to levels in the liver. The gene expression in the spleen was significantly higher (*P<0.05) when compared with all the other tissues. FIG. 13B depicts a graph of expression of GDF11 in the spleen harvested from young (3 months old) and old (24 months old) mice. Real-time PCR transcript measurements are normalized to levels in young mice. FIG. 13C depicts a graph of Western blot analysis of GDF11 in the spleen from young and old mice. Densitometry (arbitrary units, mean±s.e.m) of GDF11 normalized to α-tubulin. Data shown as mean±s.e.m.

FIG. 15A depicts a graph representing the heart weight/tibia length ratio after 30 days of treatment with rGDF11 or vehicle. The ratio in mice that were injected with rGDF11 (n=10) was not significantly different than the ratio measured in mice that were injected with vehicle (n=9) (9.08+/−0.71vs. 9.89+/−0.69 mm/mg, P=ns). FIG. 15B depicts a graph of left ventricular myocyte cross-sectional area measured after PAS staining after 30 days of treatment with rGDF11 or vehicle. Cardiomyocyte cross sectional area was not significantly different in the two groups ((286.4±12.89 μm2 in rGDF11 treated, 304.2±17.3 μm2 in vehicle treated, P=ns). FIG. 15C depicts a table with echocardiographic data after 30 days of treatment with rGDF11 or vehicle. No significant differences were noted in echocardiographic parameters of ventricular remodeling or function. AWT=anterior wall thickness; PWT=posterior wall thickness; EDD=end diastolic dimension; ESD=end systolic dimension; FS=fractional shortening. Data shown as mean±s.e.m.

DETAILED DESCRIPTION

Figure 1A:
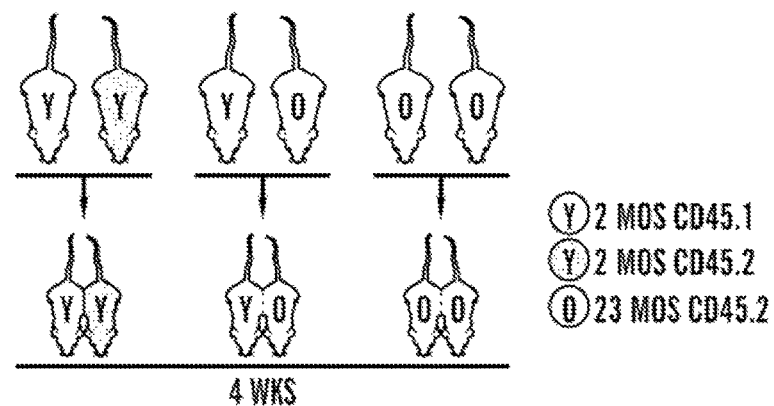
FIGS. 1A-1C demonstrate that heterochronic parabiosis reverses age-related cardiac hypertrophy.

Embodiments of the technology described herein are based on the discovery that as animals age, their level of GDF11 polypeptide decreases and results in cardiac hypertrophy. Additionally, the inventors have found that inhibiting the interaction of GDF11 and one or more follistatins can increase the level of free GDF11 in circulation. Accordingly, provided herein are methods related to Follistatin-GDF11 inhibitors, e.g. compositions which inhibit the interaction of a GDF11 polypeptide and a follistatin polypeptide. These methods and compositions relate generally to increasing the level of GDF11 polypeptide in a subject in order to treat, prevent, or reverse the conditions described herein. These methods and compositions can relate to the treatment of age-related conditions, metabolic disorders (e.g. obesity), and/or cardiac conditions including, but not limited to diastolic heart failure; cardiac hypertrophy; age-related cardiac hypertrophy; hypertension; valvular disease; aortic stenosis; genetic hypertrophic cardiomyopathy; and/or stiffness of the heart due to aging.

Described herein are methods comprising administering to a subject a composition which increases the level of GDF11 polypeptide in the subject. In some embodiments, the composition comprises a follistatin-GDF11 inhibitor. As used herein, a "follistatin-GDF11 inhibitor" refers to a molecule and/or composition that inhibits the interaction of one or more GDF11 polypeptides and one or more follistatin polypeptides. In some embodiments, the follistatin-GDF11 inhibitor inhibits the expression, secretion, and/or activity of a follistatin polypeptide. In some embodiments, the follistatin-GDF11 inhibitor inhibits the interaction of a follistatin polypeptide and a GDF11 polypeptide. In some embodiments, the follistatin can be FSTL3.

As used herein, the term "follistatin-GDF11 inhibitor" refers to an agent which can decrease the interaction of an inhibitory follistatin-GDF11 interaction (e.g. decrease follistatin-mediated inhibition of GDF11 expression, secretion, or activity and/or decrease the level of GDF11 bound to and/or by a follistatin polypeptide) e.g. by at least 10% or more, e.g. by 10% or more, 50% or more, 70% or more, 80% or more, 90% or more, 95% or more, or 98% or more. The efficacy of an inhibitor, e.g. its ability to decrease a level and/or activity can be determined, e.g. by measuring the level of a follistatin polypeptide, by measuring the level of free GDF11, and/or by measuring the level of GDF11 bound to/by a follistatin polypeptide.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons. In some embodiments, the inhibitor can be an inhibitory nucleic acid; an antibody reagent; an antibody; or a small molecule.

In some embodiments, the follistatin-GDF11 inhibitor inhibits the expression, secretion, and/or activity of a follistatin polypeptide. Methods for measuring the level of a follistatin mRNA and/or polypeptide are known to one of skill in the art, e.g. RTPCR with primers can be used to determine the level of a follistatin RNA and Western blotting with an anti-follistatin antibody (e.g. anti-FSTL3, Cat No. ab86055; Abcam; Cambridge, Mass.) can be used to determine the level of a follistatin polypeptide. Where the transcript sequences of follistatins are known, as described below herein, one of ordinary skill in the art can readily design primers for determining the level of a follistatin polypeptide.

In some embodiments, the follistatin-GDF11 inhibitor inhibits the interaction of GDF11 and one or more follistatin polypeptides. In some embodiments, the inhibitor can bind GDF11 and/or the follistatin polypeptide at or near a position where GDF11-follistatin interaction occurs, thereby blocking and/or sterically inhibiting follistatin-GDF11 interaction. In some embodiments, the inhibitor can be a small molecule. In some embodiments, the inhibitor can be an antibody.

In some embodiments, the inhibitor can be an antibody reagent, e.g. a monoclonal antibody that binds specifically to GDF11. In some embodiments, an antibody reagent that binds specifically to GDF11 does not bind to myostatin. In some embodiments, the monoclonal antibody reagent can be humanized. In some embodiments, the monoclonal antibody reagent does not interfere with the binding of GDF11 to cell surface receptors. In some embodiments, the antibody reagent binds specifically to an epitope comprised by SEQ ID NO: 15 (e.g. NMLYFNDKQQIIYGK, located at positions 381-395 of the mature GDF11). In some embodiments the antibody reagent binds specifically to an epitope comprised by SEQ ID NO: 16 (e.g. SGQCEYMFMQKYPHT, located at positions 342-356 of mature GDF11).

In some embodiments, a follistatin-GDF11 inhibitor can be a can be an inhibitory nucleic acid that inhibits the expression of a follistatin gene. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part of the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of a follistatin gene. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[$(CH_2)_nO]_mCH_3$, O$(CH_2)_nOCH_3$, O$(CH_2)_2$—$NH_2$, O$(CH_2)_nCH_3$, O$(CH_2)$—$ONH_2$, and O$(CH_2)$—ON[$(CH_2)$—$CH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$, also described in examples herein below.

Other modifications include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim Biophys. Acta, 1995, 1264:229-237), or an octadecylamine or hexylamino-carbonyloxycholesterol moiety (Crooke et al., J. Pharmacol. Exp. Ther., 1996, 277:923-937).

In some embodiments, a follistatin-GDF11 inhibitor can be an antibody reagent, e.g. an antibody that binds follistatin molecules at the GDF11 interaction sight and/or binds follistatin molecules in a way that sterically inhibits GDF11 interactions. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a follistatin.

In some embodiments, the subject is one who has, or has been diagnosed as having an age-related condition. As used herein, the term "age-related condition" refers to any disease, disorder, or undesirable state whose incidence in a population or severity in an individual correlates with the progression of age. In some embodiments, the age-related condition is a cardiovascular condition; aging of the heart; aging of skeletal muscle; or aging of the brain. Aging of any given organ can include, but is not limited to, reduced cellularity, reduced stem cell genomic integrity, reduced cellular function (e.g. reduced muscle contraction in muscle tissue), reduced regenerative capacity, atrophy (e.g. aging of the skin can include atrophy of the epidermis and/or sebaceous follicles). An age-related condition can be one that reduces the function of a given organ or one that is aesthetically undesirable (e.g. aging of the skin or muscle can be aesthetically undesirable). Additional age-related conditions can include, but are not limited to: sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

The inventors have further discovered that aged mice which have received treatments to increase free GDF11 levels show changes in adipocyte biology (e.g. reduced leptin expression), reduced appetite, and decreased weight gain. In some embodiments, the subject is one who has, or has been diagnosed as having a metabolic disorder. "Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present invention include, but are not limited to, Type II Diabetes, Metabolic Syndrome, hyperglycemia, and obesity.

In some embodiments, the composition which increases the level of GDF11 polypeptide is administered to a subject who has or has been diagnosed with diastolic heart failure, cardiac hypertrophy, age-related cardiac hypertrophy, hypertension, valvular disease, aortic stenosis, genetic hypertrophic cardiomyopathy, and/or stiffness of the heart due to aging.

In some embodiments, the level of GDF11 polypeptide is the level of GDF11 in the circulation of a subject. In some embodiments, the level of GDF11 polypeptide is the level of GDF11 in the cardiac tissue of a subject. In some embodiments, the level of GDF11 polypeptide increased by the methods described herein is the level of free GDF11, e.g. the level of GDF11 not bound to and/or by a follistatin polypeptide (e.g. FSTL3).

In some embodiments, the level of GDF11 polypeptide is determined by measuring the level of an mRNA encoding a GDF11 polypeptide. The level of GDF11 in a subject can be determined by obtaining a biological sample from the subject and determining the level of GDF11 in the biological sample. Methods for determining the level of a polypeptide in a subject or a sample obtained from a subject are well known in the art and include, but are not limited to, ELISA, radioimmunoassay, immunohistochemistry, methods involving a labeled antibody specific for GDF11, dot blot analysis, Northern blot, in-situ hybridization, and RT-PCR, among others. Antibodies specific for GDF11 are commercially available, e.g. Cat. No. ab71347 from Abcam; Cambridge, Mass., In some embodiments, the level of GDF11 can be measured as described in Souza et al, Molecular Endocrinology 2008 22:2689-2702; which is incorporated by reference herein in its entirety. Determining the level of GDF11 which is complexed with a follistatin polypeptide is within the skill of one of the art and can be measured, e.g. by co-IP, sequential or concurrent use of anti-GDF11 and anti-follistatin antibodies, etc.

As animals age, cardiac tissues often experience a decrease in diastolic function related to a thickening and/or stiffening of the tissue or cardiac hypertrophy. As used herein, the term "cardiac hypertrophy" refers to an enlargement of the heart due in part to an increase in the size of the myocytes. In some embodiments, the myocytes respond to stress through hypertrophic growth. Cardiac hypertrophy is often associated with increased risk of morbidity and mortality. In some embodiments, the cardiac hypertrophy is left ventricle cardiac hypertrophy. The term "left ventricle cardiac hypertrophy" refers to a disorder in which the myocardial tissue of the left ventricle of the heart thickens. Without wishing to be bound by theory, causes of left ventricle cardiac hypertrophy include, for example, hypertension (e.g., high blood pressure), stenosis of the aortic valve (e.g., the inability of the heart valve to fully open), and hypertrophic cardiomyopathy (e.g., a disorder in which the myocardial tissue thickens for no obvious cause). In other embodiments, the cardiac hypertrophy is right ventricle cardiac hypertrophy. The term "right ventricle cardiac hypertrophy" refers to a disorder in which the myocardial tissue of the right ventricle thickens. Without wishing to be bound by theory, causes of right ventricle hypertrophy include, for example, diseases that damage the lungs, such as emphysema and cystic fibrosis; conditions that decrease oxygen levels in the body, such as chronic bronchitis and sleep apnea; stenosis of the pulmonic heart valve, chronic pulmonary embolism, primary pulmonary hypertension, asymmetric septal hypertrophy, and idiopathic hypertrophic subaortic stenosis.

Symptoms of cardiac hypertrophy and methods of measuring them are well known in the art and include but are not limited to, an increase in left ventricular mass; a change in body weight ratio; changes in cardiomyocyte size, mass, and organization, changes in cardiac gene expression; changes in cardiac function (e.g. diastolic heart function); fibroid deposition; changes in dP/dT, i.e., the rate of change of the ventricular pressure with respect to time; calcium ion flux; stroke length; and ventricular output. Diagnostic procedures useful in detecting cardiovascular conditions and/or efficacy of treatment of cardiovascular conditions include echocardiography (e.g. 2 and 3 dimensional), MRI (e.g. spin-echo MRI or cine magnetic resonance angiography), chest radiography, thallium-201 myocardial imaging, PET, ECG-gated CT, cardiac catheterization, angiography, electrophysiological studies, and magnetic resonance spectroscopy. For example, echocardiography can detect the size of the heart, the pattern of hypertrophy, the contractile function of the heart, and the severity of the outflow gradient while MRI can evaluate ventricular anatomy, wall thickness, ventricular function, ventricular end-diastolic and end-systolic volumes, valvular dysfunction, and outflow tract obstruction.

The methods and compositions described herein relate to increasing the level of GDF11 polypeptide in a subject. As used herein, "GDF11" refers to "Growth and Differentiation Factor 11" (NCBI Gene ID No: 10220; mRNA (SEQ ID NO: 3)), a member of the Transforming Growth Factor-beta superfamily of growth factors. GDF11 is known to bind TGFβ superfamily type I receptors including ALK4, ALK5, and ALK7. For signaling in mammalian development, GDF11 predominantly uses ALK4 and ALK5. In some embodiments, GDF11 signaling can also occur via the ACVR2B receptor. GDF11 is also closely related to GDF8 (also known as myostatin). GDF11 can also be referred to as bone morphogenic protein 11, i.e. BMP11. As used herein, "GDF11" can include the human precursor polypeptide (SEQ ID NO: 1, NCBI Ref Seq: NP_005802); the human pro-peptide (SEQ ID NO: 2); the human N-terminal polypeptide (SEQ ID NO: 9), and the human mature (SEQ ID NO: 8) forms of GDF11 as well as homologs from other species, including but not limited to bovine, dog, cat, chicken, murine, rat, porcine, ovine, turkey, horse, fish, baboon and other primates. The terms also refer to fragments or variants of GDF11 that maintain at least 50% of the cardiac hypertrophy-reducing (or prevention) effect of the full length GDF11 of SEQ ID NO: 2, SEQ ID NO: 1, or SEQ ID NO: 8. e.g. as measured in an appropriate animal model. Conservative substitution variants that maintain cardiac hypertrophy-reducing or preventing activity of wildtype GDF11 will include a conservative substitution as defined herein. The identification of amino acids most likely to be tolerant of conservative substitution while maintaining at least 50% of the activity of the wildtype is guided by, for example, sequence alignment with GDF11 homologs or paralogs from other species. Amino acids that are identical between GDF11 homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model with cardiac hypertrophy and imaging as described herein to follow any reversion of the hypertrophy.

For human GDF11, the pro-peptide plus signal sequence (e.g. the precursor polypeptide) is 407 amino acids long. Cleavage of the 24 amino acid signal peptide generates a pro-peptide of 383 amino acids and cleavage of the pro-peptide results in a mature GDF11 polypeptide of 109 amino acids that corresponds to the C-terminal 109 amino acids of the pro-peptide. The mature polypeptide forms a disulfide-linked homodimer. Cleavage of the pro-peptide also generates the N-terminal polypeptide (e.g. SEQ ID NO: 9) comprising amino acids 25-298 of SEQ ID NO: 1. The N-terminal GDF11 polypeptide can antagonize the activity of e.g. the polypeptides of SEQ ID NOs: 2 and 8, at least in vitro by forming: a complex with the other forms of GDF11 polypeptides and can thus be used to modulate the activity of GDF11 compositions as described herein. Thus, to the extent that GDF11 polypeptides as described herein reduce or prevent cardiac conditions, e.g., cardiac hypertrophy or stiffening among others, and to the extent the N-terminal GDF11 polypeptide of, e.g., SEQ ID NO: 9, can antagonize such reduction or prevention, the polypeptide of SEQ ID NO: 9 can be excluded from the meaning of "GDF11 polypeptide" as that term is used herein.

The methods and compositions described herein can relate to a follistatin-GDF11 inhibitor. As used herein, "follistatin" refers to one or more members of the follistatin/follistatin-like family of proteins. Follistatins are activin-binding proteins with an FS module (a conserved sequence comprising 10 conserved cysteine residues). Follistatins can include, e.g. FST, FSTL1, FSTL2, FSTL3, FSTL4, and/or FSTL5. In some embodiments, a follistatin can be FSTL3. The sequences of follistatin genes, mRNAs, and polypeptides for a variety of species are well known in the art, e.g. human FSTL3 (NCBI Gene ID NO: 10272) (SEQ ID NO: 10, NCBI Ref Seq: NM_005860)(SEQ ID NO: 11, NCBI Ref Seq: NP_005851).

TABLE 3

| Follistatin | mRNA NCBI Ref Seq | Polypeptide NCBI Ref Seq |
| --- | --- | --- |
| FST | NM_013409 | NP_037541 |
| FSTL1 | NM_007085 | NP_009016 |
| FSTL2 | NM_001253835 | NP_001240764 |
| FSTL3 | NM_005860 | NP_005851 |
| FSTL4 | NM_015082 | NP_055897 |
| FSTL5 | NM_020116 | NP_064501 |

As used herein, the terms "proteins" and "polypeptides" are used interchangeably to designate a series of amino acid residues connected to the other by peptide bonds between the alpha-amino and carboxy groups of adjacent residues. The terms "protein", and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. As used herein, "pro-peptide" used in reference to GDF11 refers to a GDF11 polypeptide in which the signal domain (e.g. amino acids 1-24 of SEQ ID NO:1) which has been cleaved off during formation of the mature and/or active forms of GDF11. As used herein, "precursor peptide" used in reference to GDF11 refers to a GDF11 polypeptide comprising the signal domain, e.g. a polypeptide comprising the amino acid sequence of SEQ ID NO: 1.

In some embodiments, a follistatin-GDF11 inhibitor as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs,* [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", Adv. *Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", Adv. *Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.,* 39(1-3):63-80 (1999); Waller et al., "Prodrugs", *Br. J. Clin. Pharmac.* 28: 497-507 (1989), which are incorporated by reference herein in their entireties.

In some embodiments, a follistatin-GDF11 inhibitor as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a follistatin-GDF11 inhibitor as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid encoding a follistatin-GDF11 inhibitor as described herein is comprised by a vector. In some of the aspects described herein, a nucleic acid sequence encoding a follistatin-GDF11 inhibitor as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a follistatin-GDF11 inhibitor as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments the level of GDF11 in the subject is increased by at least 20% over the level of GDF11 in the subject prior to treatment, e.g. 20% or more, 30% or more, 40% or more, 50% or more, 100% or more, 150% or more, 200% or more, 250% or more, 300% or more, or 350% or more. In some embodiments the level of GDF11 in the subject is increased by at least 100% over the level of GDF11 in the subject prior to treatment. In some embodiments the level of GDF11 in the subject is increased by at least 200% over the level of GDF11 in the subject prior to treatment. In some embodiments the level of GDF11 in the subject is increased by about 250% over the level of GDF11 in the subject prior to treatment. In some embodiments, the level of GDF11 in the subject is increased to at least 50% of a healthy reference level, e.g. 50% or more, 60% or more, 70% or more, 80% or more, 90% or more, or 100% or more of a healthy reference level. In some embodiments, the level of GDF11 in the subject is increased to at least 60% of a healthy reference level. In some embodiments, the level of GDF11 in the subject is increased to at least 75% of a healthy reference level. In some embodiments, the level of GDF11 in the subject is increased to at least 90% of a healthy reference level. A healthy reference level can be the average level of GDF11 in a population of human subjects not exhibiting any signs or symptoms of cardiac hypertrophy, diastolic heart failure, or related conditions. In some embodiments, the level of GDF11 which is increased is the level of free GDF11.

In some embodiments, a healthy reference level can be the average level of GDF11 in a population of human subjects not exhibiting any signs or symptoms of cardiac hypertrophy, diastolic heart failure, or related conditions and who are under the age of 70. In some embodiments, a healthy reference level can be the average level of GDF11 in a population of human subjects not exhibiting any signs or symptoms of cardiac hypertrophy, diastolic heart failure, or related conditions and who are under the age of 65. In some embodiments, a healthy reference level can be a level equivalent to at least 8,500 units as measured by the aptamer technology described in the Examples herein, e.g. 8,500 or greater, 9,000 or greater, or 10,000 or greater.

In some embodiments, the methods described herein can comprise selecting a subject with a level of GDF11 which is lower than a healthy reference level and administering a treatment as described herein.

In some embodiments, the level of GDF11 in a subject is increased in order to treat a cardiac condition, e.g. cardiac hypertrophy or stiffening as described herein. In some embodiments, the level of GDF11 in a subject is increased in order to prevent a cardiac condition, e.g. cardiac hypertrophy or stiffening as described herein. Cardiac conditions related to low or decreased GDF11 polypeptide tend to develop with the decrease in GDF11 levels that occur with increasing age. Thus, it is expected that such conditions can be prevented or, at a minimum, delayed, by maintaining GDF11 polypeptide levels at or near the level found in normal, healthy young adults, e.g. by administering a GDF11 polypeptide or a nucleic acid encoding a GDF11 polypeptide with advancing age, but prior to the onset of a cardiac disorder.

Aspects of the technology described herein relate to compositions comprising a follistatin-GDF11 inhibitor as described herein. In some embodiments, the composition is a pharmaceutical composition. As used herein, the term "pharmaceutical composition" refers to the active agent in combination with a pharmaceutically acceptable carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and generally need not be limited based on formulation. Typically such compositions are prepared as injectable either as liquid solutions or suspensions, however, solid forms suitable for solution, or suspension, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents, and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, a follistatin-GDF11 inhibitor as described herein can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled-release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the technology described herein relates to a syringe comprising a therapeutically effective amount of a composition e.g. a pharmaceutical preparation comprising a follistatin-GDF11 inhibitor as described herein.

As used herein, the phrase "therapeutically effective amount", "effective amount" or "effective dose" refers to an amount that provides a therapeutic or aesthetic benefit in the treatment, prevention, or management of, for example, cardiac hypertrophy, e.g. an amount that provides a statistically significant decrease in at least one symptom, sign, or marker of cardiac hypertrophy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In one aspect, the technology described herein relates to a method comprising administering a follistatin-GDF11 inhibitor to a subject. In some embodiments, the subject is in need of treatment for cardiac hypertrophy, diastolic heart failure or a related condition as described above herein. In some embodiments, the method is a method of treating a subject. In some embodiments, the method is a method of treating cardiac hypertrophy and/or diastolic heart failure or a related condition in a subject. Such conditions, as well as methods of diagnosing them are described above herein.

As used herein, the terms "treat" "treatment" "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of, for example, cardiac hypertrophy, delay or slowing of cardiac hypertrophy, and an increased lifespan as compared to that expected in the absence of treatment.

As used herein, the term "administering," refers to the placement of the composition comprising a follistatin-GDF11 inhibitor as disclosed herein into a subject by a method or route which results in delivery to a site of action. The pharmaceutical composition comprising a follistatin-GDF11 inhibitor can be administered by any appropriate route which results in an effective treatment in the subject.

Data described herein indicate that systemic administration via the vascular system can be effective. Thus administration via the intravenous route is specifically contemplated. However, with appropriate formulation, other routes are contemplated, including, for example, intranasally, intra-arterially; intra-coronary arterially; orally, by inhalation, intraperitoneally, intramuscularly, subcutaneously, intracavity, or by other means known by those skilled in the art. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The dosage ranges for the agent depends upon the potency, and are amounts large enough to produce the desired effect e.g., a decrease of the rate of cardiac hypertrophy or a reversal of cardiac hypertrophy. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. Typically, the dosage can range from 0.001 mg/kg body weight to 0.5 mg/kg body weight. In one embodiment, the dose range is from 5 µg/kg body weight to 30m/kg body weight.

Administration of the doses recited above can be repeated. In some embodiments, the doses are given once a day, or multiple times a day, for example, but not limited to, three times a day. In some embodiments, the doses recited above are administered daily for weeks or months. The duration of treatment depends upon the subject's clinical progress and responsiveness to therapy. Where the GDF11 polypeptide apparently diminishes with age in affected individuals, it is expected that long-term therapy would be required to establish and maintain the benefit of GDF11-based treatment, e.g. for cardiac hypertrophy.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent administration. Alternatively, continuous intravenous infusion sufficient to maintain concentrations in the blood in the ranges specified for in vivo therapies are contemplated. In some embodiments, the dosage range is sufficient to maintain concentrations in the blood in the range found in the blood of a population of normal, healthy human subjects (e.g. those with no signs, symptoms, or makers of cardiac hypertrophy) under the age of 50. In some embodiments, the dosage range is sufficient to maintain concentrations in the blood in the range found in normal, healthy human subjects under the age of 40. In some embodiments, the dosage range is sufficient to maintain concentrations in the blood in the range found in normal, healthy human subjects under the age of 30.

A therapeutically effective amount is an amount of an agent that is sufficient to produce a statistically significant, measurable change in, for example, cardiac hypertrophy. Such effective amounts can be gauged in clinical trials as well as animal studies. Efficacy of an agent can be determined by assessing physical indicators of, for example cardiac hypertrophy as described above herein. In experimental systems, assays for efficacy include measurement of heart mass as well as, determination of myocyte size as determined by histological microscopy, and/or a reduction in expression of aged myocardium marker genes such as ANP and BNP. Such assays are well known in the art and described in detail in the Examples herein. Clinically acceptable methods for detecting or monitoring cardiac hypertrophy are described herein below. In addition, efficacy of an agent can be measured by an increase in GDF11 polypeptides or fragments thereof in a subject being treated with a follistatin-GDF11 inhibitor.

The efficacy of a given treatment for cardiac hypertrophy can be determined by the skilled clinician. However, a treatment is considered "effective treatment," as the term is used herein, if any one or all of the signs or symptoms of e.g., cardiac hypertrophy are altered in a beneficial manner, other clinically accepted symptoms are improved or ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein. The extent and severity of cardiac hypertrophy and/or the efficacy of a treatment for cardiac hypertrophy can be determined by imaging of the heart to gauge hypertrophy, e.g. using MRI or 2-dimensional echocardiography. Imaging of cardiac hypertrophy is described in more detail in Agarwal and Hartnell "Imaging in Hypertrophic Cardiomyopathy" Medscape Reference, May 27, 2011 (available online at http://emedicine.medscape.com/article/348503-overview); which is incorporated by reference herein in its entirety.

In some embodiments, the methods further comprise administering the pharmaceutical composition described herein along with one or more additional agents, biologics, drugs, or treatments beneficial to a subject suffering from cardiac hypertrophy or diastolic heart failure as part of a combinatorial therapy. In some such embodiments, the agent, biologic, drug, or treatment can be selected from the group consisting of: treatments for high blood pressure (e.g. thiazide diuretics; ACE inhibitors such as enalapril, lisinopril, and captropril; ARBs such as losartan or valsartan; beta blockers such as atenolol, carvedilol, metoprolol and bisoprolol; calcium channel blockers such as amlodipine, diltiazem, nifedipine, and verapamil); aortic valve repair; treatments to relax the muscle or slow the rate of muscle contraction (e.g. beta blockers, calcium channel blockers, or anti-arrhythmic treatments such as disopyramide or amiodarone); septal myectomy; septal ablation; pacemaker implantation; and/or cardioverter-defibrillator implantation.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "cardiovascular condition" refers to a condition mediated or characterized by a reduction in circulating GDF11 polypeptide. Non-limiting examples of cardiovascular conditions include diastolic heart failure; cardiac hypertrophy; hypertension; valvular disease; aortic stenosis; genetic hypertrophic cardiomyopathy; or stiffness of the heart due to aging.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased","increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or more as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

The term "biological sample" as used herein denotes a sample taken or isolated from a biological organism, e.g., cardiac biopsy sample, blood sample, cell lysate, a homogenate of a tissue sample from a subject, or a fluid sample from a subject. Exemplary biological samples include, but are not limited to, cardiac tissue biopsies or blood and/or serum samples. In some embodiments, the sample is from a resection, biopsy, or core needle biopsy. In addition, fine needle aspirate samples can be used. Samples can include paraffin-embedded and frozen tissue. The term "biological sample" also includes untreated or pretreated (or pre-processed) biological samples. In some embodiments, the biological sample is an untreated biological sample. The sample can be obtained by removing a sample of cells from a subject, but can also be accomplished by using previously isolated cells (e.g. isolated at a prior timepoint and isolated by the same or another person."

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, cardiac hypertrophy. In addition, the methods described herein can be used to treat domesticated animals and/or pets. A subject can be male or female.

A subject can be one who has been previously diagnosed with or identified as suffering from or having a condition in need of treatment (e.g. cardiac hypertrophy) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition. A "subject in need" of treatment for a particular condition can be a subject having that condition, diagnosed as having that condition, or at increased risk of developing that condition relative to a given reference population.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (Ellington et al. Nature. 1990; 346(6287):818-822; Tuerk et al., Science. 1990; 249(4968):

505-510; Ni et al., Curr Med Chem. 2011; 18(27):4206-14; which are incorporated by reference herein in their entireties). Methods of generating an apatmer for any given target are well known in the art. Preclinical studies using, e.g. aptamer-siRNA chimeras and aptamer targeted nanoparticle therapeutics have been very successful in mouse models of cancer and HIV (Ni et al., Curr Med Chem. 2011; 18(27): 4206-14).

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described for example in Sambrook et al., Molecular Cloning: A Laboratory Manual (4 ed.), Cold Spring Harbor Laboratory Press, Cold Spring Harbor, N.Y., USA (2012) and Davis et al., Basic Methods in Molecular Biology, Elsevier Science Publishing, Inc., New York, USA (1995) which are both incorporated by reference herein in their entireties.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A method of treating an age-related condition, the method comprising administering to a subject a follistatin-GDF11 inhibitor.
2. The method of paragraph 1, wherein the age-related condition is selected from the group consisting of:
    a cardiovascular condition; aging of the heart; aging of skeletal muscle; aging of the brain; a metabolic disorder; and obesity.
3. The method of any of paragraphs 1-2, wherein the subject has or has been diagnosed with a condition selected from the group consisting of:
    diastolic heart failure; cardiac hypertrophy; age-related cardiac hypertrophy; hypertension; valvular disease; aortic stenosis; genetic hypertrophic cardiomyopathy; or stiffness of the heart due to aging.
4. The method of any of paragraphs 1-3, wherein the level of GDF11 polypeptide in the subject is increased.

5. The method of paragraph 4, wherein in the level of GDF11 polypeptide is the level of free GDF11.
6. The method of paragraph 4, wherein the level of GDF11 polypeptide is the level of GDF11 in the circulation of the subject.
7. The method of paragraph 4, wherein the level of GDF11 polypeptide is the level of GDF11 in the cardiac tissue of the subject.
8. The method of any of paragraphs 1-7, wherein the follistatin-GDF11 inhibitor comprises an inhibitory nucleic acid; an antibody reagent; an antibody; or a small molecule.
9. The method of any of paragraphs 1-8, wherein the follistatin-GDF11 inhibitor comprises an antibody reagent that binds specifically to an epitope comprised by SEQ ID NO: 15 or SEQ ID NO: 16.
10. The method of paragraph 9, wherein the antibody reagent is selected from the group consisting of:
a humanized antibody reagent; a monoclonal antibody; and a humanized monoclonal antibody.
11. The method of any of paragraphs 1-10, wherein the composition is administered via a route selected from the group consisting of:
intravenously; subcutaneously; intra-arterial; and intra-coronary arterial.
12. The method of any of paragraphs 1-11, wherein the level of GDF11 is increased by at least 100%.
13. The method of any of paragraphs 1-11, wherein the level of GDF11 is increased to at least 75% of a healthy reference level.
14. A pharmaceutical composition comprising an isolated follistatin-GDF11 inhibitor and a pharmaceutically acceptable carrier.
15. The use of a follistatin-GDF11 inhibitor for the treatment of a condition selected from the group consisting of:
a cardiovascular condition; aging of the heart; aging of skeletal muscle; aging of the brain; diastolic heart failure; cardiac hypertrophy; age-related cardiac hypertrophy; hypertension; valvular disease; aortic stenosis; genetic hypertrophic cardiomyopathy; stiffness of the heart due to aging; obesity; and a metabolic disorder.
16. The use of paragraph 15, wherein the level of GDF11 polypeptide in the subject is increased.
17. The use of paragraph 16, wherein in the level of GDF11 polypeptide is the level of free GDF11.
18. The use of paragraph 16, wherein the level of GDF11 polypeptide is the level of GDF11 in the circulation of the subject.
19. The use of paragraph 16, wherein the level of GDF11 polypeptide is the level of GDF11 in the cardiac tissue of the subject.
20. The use of any of paragraphs 15-19, wherein the follistatin-GDF11 inhibitor comprises an inhibitory nucleic acid; an antibody reagent; an antibody; or a small molecule.
21. The use of any of paragraphs 15-20, wherein the follistatin-GDF11 inhibitor comprises an antibody reagent that binds specifically to an epitope comprised by SEQ ID NO: 15 or SEQ ID NO: 16.
22. The use of paragraph 21, wherein the antibody reagent is selected from the group consisting of:
a humanized antibody reagent; a monoclonal antibody; and a humanized monoclonal antibody.
23. The use of any of paragraphs 15-22, wherein the composition is administered via a route selected from the group consisting of:
intravenously; subcutaneously; intra-arterial; and intra-coronary arterial.
24. The use of any of paragraphs 15-23, wherein the level of GDF11 is increased by at least 100%.
25. The use of any of paragraphs 15-23, wherein the level of GDF11 is increased to at least 75% of a healthy reference level.

EXAMPLES

Example 1

Identification of Growth Differentiation Factor 11 as a Circulating Factor that Reverses Age-Related Cardiac Hypertrophy The most common form of heart failure occurs with normal systolic function, has no specific treatment and often involves cardiac hypertrophy in the elderly. To clarify the biological mechanisms that drive cardiac hypertrophy in aging, the influence of circulating factors was tested using heterochronic parabiosis, a surgical technique in which joining of animals of different ages leads to a shared circulation. After 4 weeks of exposure to the circulation of young mice, cardiac hypertrophy in old mice dramatically regressed, accompanied by reduced cardiomyocyte size and molecular remodeling. Reversal of age-related hypertrophy was not attributable to hemodynamic or behavioral effects of parabiosis, implicating a blood-borne factor. Using modified aptamer-based proteomics, the TGFβ superfamily member GDF11 was identified as a circulating factor in young mice that declines with age. Treatment of old mice to restore GDF11 to youthful levels recapitulated the effects of parabiosis and reversed age-related hypertrophy, providing a new therapeutic opportunity for cardiac aging.

Among the diseases and disorders associated with advancing age, one of the most debilitating is the loss of normal cardiac function leading to heart failure. Heart failure affects approximately 1% of individuals over 50 and over 5% of individuals over 75. With the ongoing steep rise in the proportion of elderly individuals within our population (Schocken et al., 2008), age-related heart failure is becoming increasingly prevalent.

Most age-related heart failure occurs in the setting of normal systolic function. This condition is often associated with cardiac hypertrophy and called "diastolic heart failure", in contrast to "systolic heart failure" (Aurigemma, 2006). Although progress has been made in the treatment of systolic heart failure, with substantial improvements in outcome over the past two decades, progress in treating diastolic heart failure has been much more elusive (Hunt et al., 2009). Indeed, one can argue that there are no specific therapies for patients who experience the ventricular "stiffening" associated with the diastolic dysfunction that accompanies aging (Kitzman and Daniel, 2007).

Emerging evidence indicates that systemic factors profoundly influence tissue aging. Some of these data have emerged from the experimental model of parabiosis, which was first developed in the 19th century (Finerty, 1952). In parabiosis, two mice are surgically joined, such that they develop a shared blood circulation with rapid and continuous exchange of cells and soluble factors at physiological levels through their common circulatory system (Wright et al., 2001). The pair of animals may be the same age (isochronic parabionts) or different ages (heterochronic parabionts). Because parabiotic mice are connected solely through their common circulation, parabiosis is a powerful model to determine whether circulating factors can alter tissue function (Balsam et al., 2004; Brack et al., 2007; Conboy et al., 2005; Eggan et al., 2006; Ruckh et al., 2012; Sherwood et al., 2004; Villeda et al., 2011; Wagers et al., 2002; Wright et al., 2001). Heterochronic parabiosis experiments suggest that blood-borne signals from a young circulation can significantly impact the function of aging tissues, as indicated by the restoration of appropriate activation and function of endogenous, "old" skeletal muscle satellite cells and successful muscle repair after injury following exposure to a "youthful" systemic milieu (Conboy et al., 2005). Conversely, exposing a young mouse to an old systemic environment can inhibit myogenesis (Brack et al., 2008) and neurogenesis (Villeda et al., 2011) in the young mouse.

Here, using a parabiosis model, it is demonstrated that age-related cardiac hypertrophy can be reversed by exposure to a young circulatory environment. These experiments reveal that the cardiac hypertrophy of aging is at least in part mediated by circulating factors, and led to the discovery that systemic GDF11, a TGFβ family member, can reverse age-related cardiac hypertrophy. These data indicate that at least some component of age-related heart failure is hormonal in nature and reversible.

Results

Figure 5:
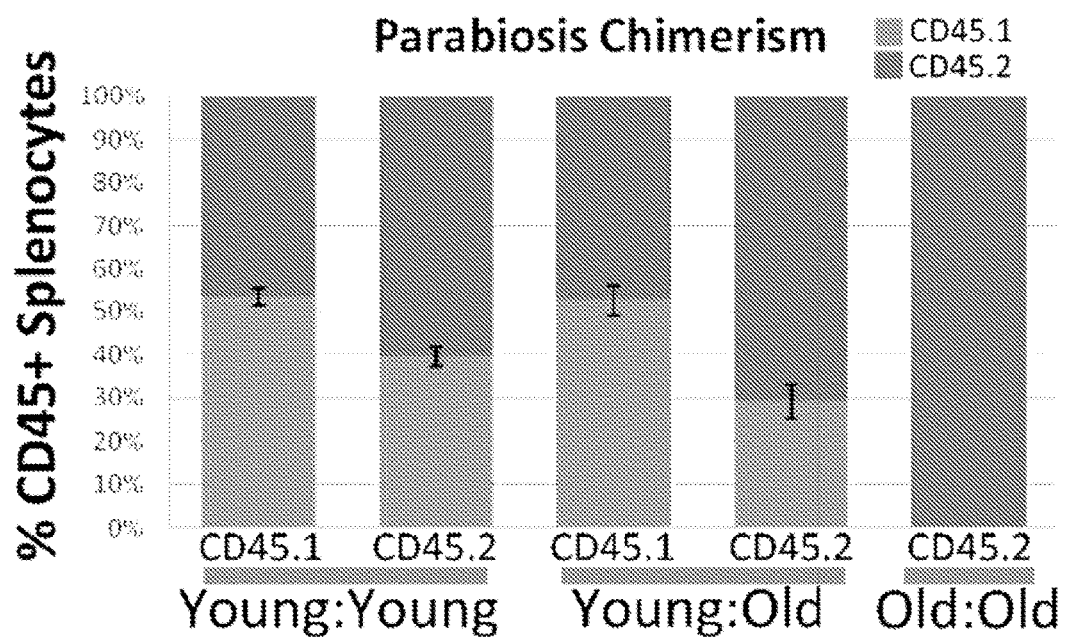
FIG. 5 depicts confirmation of chimerism. Blood chimerism was confirmed in parabiotic pairs by measuring the frequency of donor-derived blood cells from one partner (CD45.1+) in the spleen of the other partner (CD45.2+). Partner-derived cells typically represented 40-50% of splenocytes, consistent with establishment of parabiotic cross-circulation. Because old CD45.1+ mice are not commercially available it was not possible to verify the establishment of chimerism in old parabiotic pairs; however, the inventors' extensive experience with this model, and unpublished data from GFP$^{young}$/WT$^{old}$ pairs strongly support the conclusion that cross-circulation is established equally effectively in these fully isogenic pairs.

Heterochronic parabiosis reverses age-related cardiac hypertrophy. The inventors hypothesized that circulating factors specific to a young mouse might reverse cardiac aging. To test this hypothesis, heterochronic parabiotic (HP) pairs were generated, in which young female C57BL/6 mice (Y-HP, 2 months) were surgically joined to old partners (O-HP, 23 months), and compared these to isochronic parabiotic (IP) pairs (young—young, Y-IP, or old—old, O-IP), joined at identical ages, and to age- and sex-matched unpaired mice as controls (young Y and old O) (FIG. 1A). Cardiac aging in C57Bl/6 mice recapitulates human cardiac aging, including development of age-related cardiac hypertrophy (Dai et al., 2009) in a gender independent fashion. Parabiotic pairs were maintained for 4 weeks before analysis, and congenic markers were used to distinguish blood cells from aged (CD45.2+) versus young (CD45.1+) partners (Wright et al., 2001). This strategy allowed blood chimerism in the pairs to be monitored; however, because old CD45.1+ mice are not commercially available, only CD45.2+ mice were used to generate isochronic old pairs. Mice were euthanized 4 weeks after joining, and cross-circulation was confirmed in most of the pairs (>90%) by measuring the frequency of donor-derived blood cells from one partner (CD45.1+) in the blood or spleen of the other partner (CD45.2+) (FIG. 5).

Figure 1B:
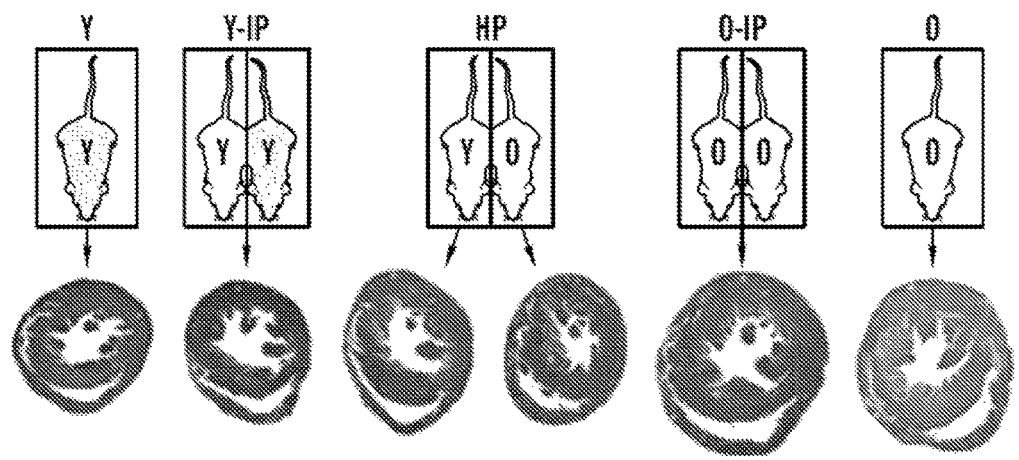
Figure 1C:
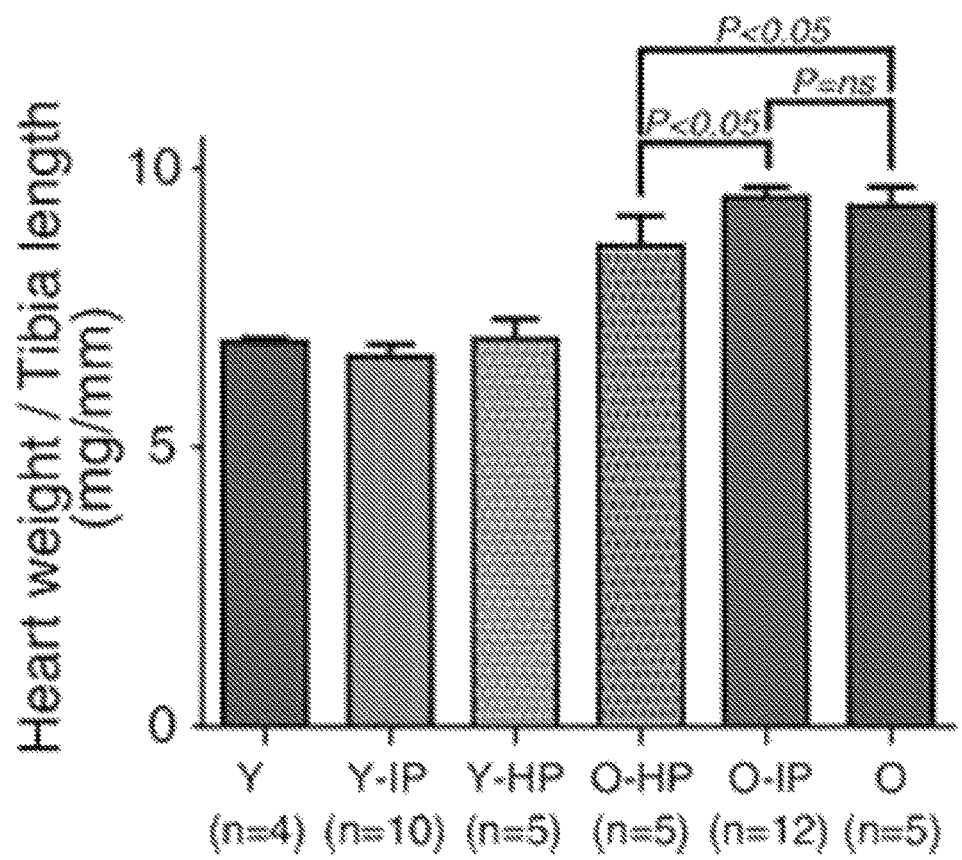

The striking effect of a young circulation on old hearts was immediately apparent on visual inspection. Hearts from old mice exposed to a young circulation (O-HP) for 4 wks were noticeably smaller than hearts from O-IP mice. This observation was confirmed by a blinded comparison of short-axis histological sections taken from the midventricle (FIG. 1B). The hearts were weighed at the time of sacrifice and cardiac mass normalized to tibia length, a standard method that corrects for differences in body frame size (Yoshioka et al., 2007) and that is more appropriate than normalization to body weight when using older mice (Jackson et al., 2012; Yin et al., 1982). The heart weight to tibia length ratio was significantly lower in old mice exposed to a young circulation (O-HP) compared to old mice exposed to an old circulation (O-IP), after 4 weeks of parabiosis (7.93+/−0.19 vs.9.61+/−0.21 mm/mg, P<0.05, FIG. 1C).

It was next tested if the gross regression of cardiac hypertrophy was due to changes in cellular hypertrophy by performing blinded morphometric analysis of cardiac histologic sections (data not shown). No significant difference in LV cardiac myocyte cross sectional area in young mice from any of the three experimental conditions was found (186.7±4.9 μm$^2$ in Y, 243.1±12.1 μm$^2$ in Y-IP, 232.2±16.4 μm$^2$ in Y-HP). As expected from published data (Dai et al., 2009), the average cardiac myocyte cross-sectional area was significantly greater in the hearts of the old isochronic (357.8±25.8 μm$^2$) and old non-parabiotic controls (348.3±12.6 μm$^2$) FIG. 2A). However, aging hearts from mice exposed to a young circulation for 4 wks (O-HP) showed a significant reduction in myocyte size when compared to O-IP hearts (220.4±21.9 vs. 357.8±25.8 μm$^2$, P<0.05). Thus, exposure to a young circulation reverses the hypertrophic cellular phenotype of aged hearts to the morphologic phenotype typical of a young adult mouse.

To evaluate possible sex-specific effects, these experiments were repeated using male mice, and a similar regression in age-related hypertrophy after exposure to a young circulation was observed (FIG. 2B). These data indicate that gender is not a factor in the reversal of age-related hypertrophy by a young circulation. Thus, age-dependent cardiac hypertrophy may be reversed in both males and females through the activity of systemic factors, and the striking impact of such youthful factors on this age-related pathology is apparent with only 4 weeks of parabiosis.

Figure 6A:
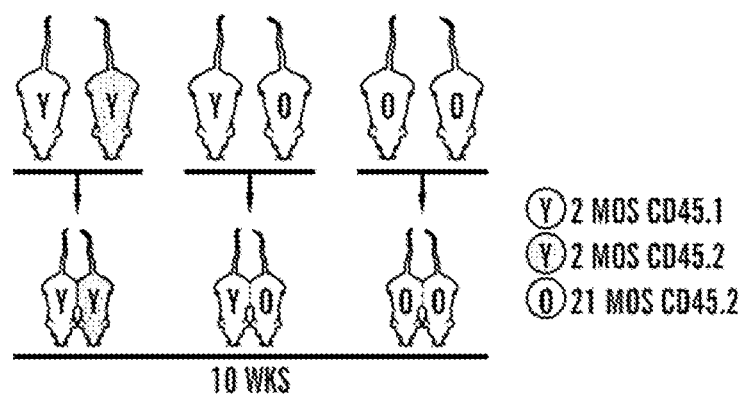
FIGS. 6A-6B depict the design of the experiment and assessment of cardiac mass.

The reversal of cardiac hypertrophy in old mice exposed to a young circulation is not explained by a reduction in blood pressure. A crucial question raised by these data is whether a hemodynamic effect may mediate the reduced cardiac hypertrophy seen in aged mice following heterochronic parabiosis. To explore the hemodynamic issue in the setting of parabiosis, female heterochronic parabiotic pairs (young, 2 months and old, 21 months) were generated and compared with equal numbers of young and old isochronic parabiotic pairs and with sex and age-matched non-parabiotic controls, using congenic markers to confirm development of cross-circulation (FIG. 6A).

Mice were joined for 10 weeks, and during this period noninvasive blood pressure measurements were performed using a computerized tail-cuff system (BP-2000, Visitech Systems, Apex, N.C.) (Krege et al., 1995) that was modified to hold parabiotic mice. In non-parabiosed controls (FIG. 3A), a significantly lower systolic blood pressure was observed in aged female mice (23 months old and 21 months old, n=32) compared to young (8 wk-old) CD45.2 females (n=12) (98.3±1.8 vs. 129.9±2.0 mmHg, P<0.05), but we saw no difference when comparing aged CD45.2 to young CD45.1 female mice (n=16) (98.3±1.8 vs. 104.1±1.9 mmHg, P=ns). There were no differences in heart rate between the groups (FIG. 3A). These data suggest that differences in blood pressure or heart rate at the time of study entry are unlikely to explain the ensuing changes in myocyte size and global ventricular mass seen in O-HP mice.

Figure 6B:
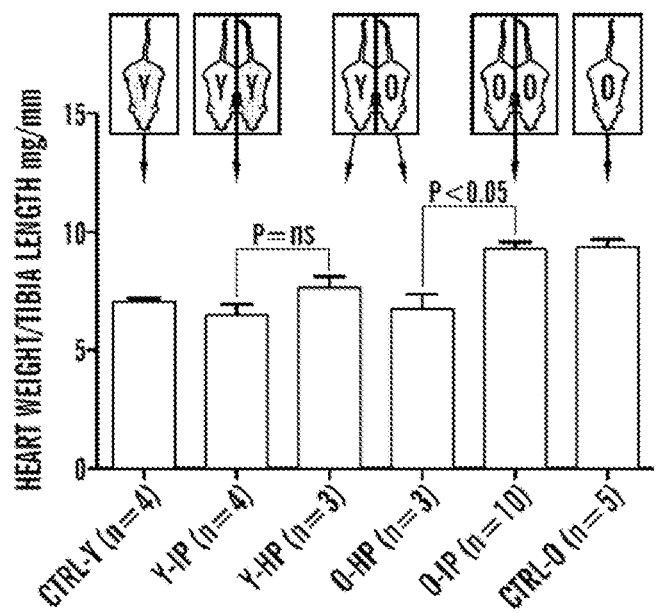

To further address the possible impact of hemodynamic changes in the parabiotic mice, noninvasive blood pressure measurements were performed at serial time points on heterochronic pairs and compared them to isochronic young and old pairs over 10 wks. No change was detected over time in the blood pressure of young mice from any of the groups (FIG. 3B). In contrast, aged mice exposed to a young circulation (O-HP) showed a significant increase in systolic blood pressure at 7 and 10 weeks, and aged members of isochronic pairs exhibited significantly increased blood pressure at 7 weeks, relative to baseline measurements. Finally, terminal intra-arterial hemodynamic tracings were obtained using simultaneous micromanometer catheterizations, performed after mice had been joined for 10 weeks. In these studies, mean arterial pressure did not differ significantly among any of the groups (FIG. 3C). Cross-circulation was confirmed after euthanasia by measuring the frequency of donor-derived blood cells from one partner (CD45.1+) in the spleen of the other partner (CD45.2+) (data not shown), and evaluation of cardiac mass confirmed that O-HP mice in this 10 week experiment also showed significant reduction in the heart weight-tibia length index when compared to the old controls (FIG. 6B). In addition, cardiac size was unaltered in young mice joined for 10 weeks to an old partner, indicating that prolonged exposure to an aged circulation did not induce hypertrophy in young mice, as might be predicted if young mice were serving as a sink for a hypertrophic factor produced by the old mice (FIG. 6B). Finally, consistent with these direct measurements of blood pressure in parabiotic mice, circulating levels of angiotensin II and aldosterone were not different in animals involved in heterochronic parabiosis as compared to their age-matched counterparts joined in isochronic parabiosis (data not shown). Thus, it is unlikely that changes in the renin-angiotensin-aldosterone (RAA) axis, well known for its ability to regulate blood pressure and volume, contribute to remodeling of the myocardium in aged heterochronic parabionts.

Taken together, these data clearly demonstrate that the observed reversal of cardiac hypertrophy in old mice exposed to a young circulation cannot be explained by a simple reduction in blood pressure or modulation of known effectors of blood pressure in the older mice. These data further implicate an anti-hypertrophic factor produced by young mice (rather than dilution of a pro-hypertrophy factor produced by old mice) in the cardiac remodeling induced by heterochronic parabiosis.

Differences in blood pressure between young CD45.1 and CD45.2 mice do not explain the reversal of cardiac hypertrophy. Because young CD45.1 mice have a significantly lower blood pressure at baseline when compared to young CD45.2 mice, the parabiosis experiments were repeated using exclusively CD45.2 mice to generate heterochronic pairs in which young CD45.2 female mice (Y-HP, 2 months) were joined to aged CD45.2 partners (O-HP, 23 months). These heterochronic mice were compared to isochronic pairs (Y-IP, 2 months, or O-IP, 23 months), after 4 weeks of parabiosis. As the mice in this experiment were genetically identical, flow cytometry could not be used to verify the establishment of chimerism in these pairs; however, extensive experience with this model strongly supports the conclusion that cross-circulation is effectively established in fully isogenic pairs (Pietramaggiori et al., 2009).

Figure 10A:
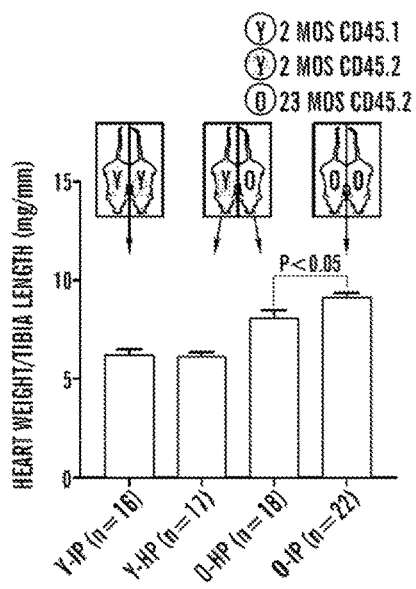
FIGS. 10A-10D demonstrate that differences in blood pressure between young CD45.1 and CD45.2 mice do not explain the reversal of cardiac hypertrophy.
Figure 10C:
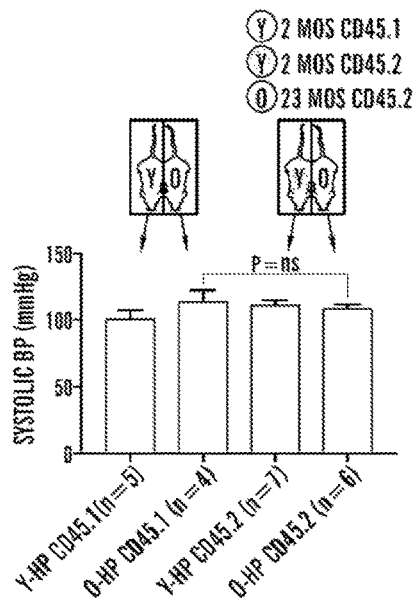
Figure 10B:
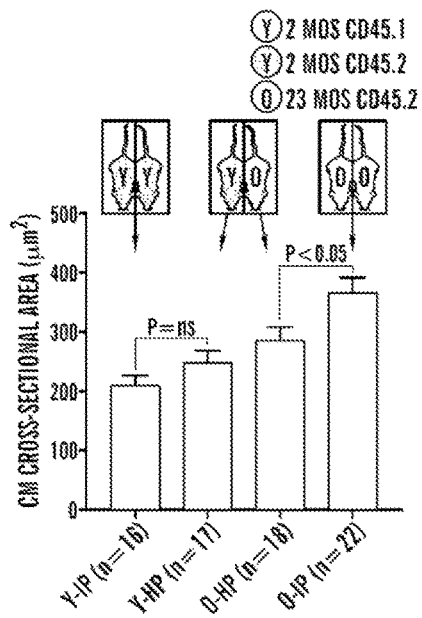
Figure 10D:
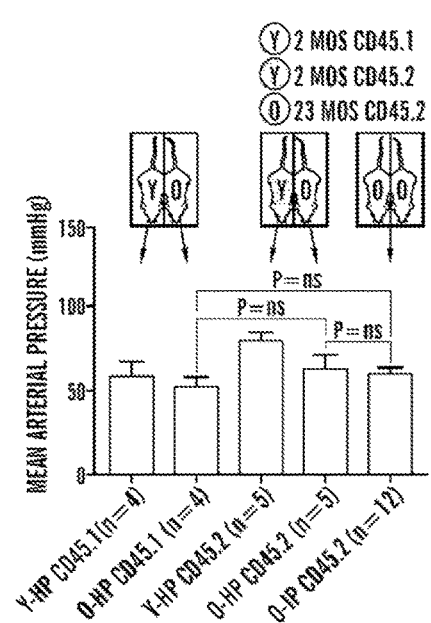

As in prior studies, exposure to the circulation of young CD45.2 mice via parabiosis led to a reduction of heart weight to tibia length ratio in O-HP CD45.2 mice (n=18) when compared to O-IP animals (n=22) (8.03+/−0.38 vs. 9.07+/−0.24 mm/mg, P<0.05, FIG. 10A). Cardiomyocyte cross-sectional area was also significantly reduced in O-HP mice when compared to O-IP (286.3±22.7 vs. 366.4±25.4 $\mu m^2$, P<0.05, FIG. 10B). Aged partners of heterochronic pairings using only CD45.2 mice also showed a blood pressure profile after 4 weeks that was comparable to O-HP mice that had been joined to young CD45.1 partners (FIG. 10C-10D). Also, similar to results obtained using CD45.1 young partners, heterochronic parabiosis induced no changes in heart weight/tibia ratio (FIG. 10A), cardiomyocyte size (FIG. 10B), or blood pressure in young CD45.2 mice joined to aged partners (FIG. 10C-10D). These data demonstrate that the regression of cardiac hypertrophy observed in old mice exposed to a young circulation cannot be explained by the blood pressure differences observed in young CD45.1 and CD45.2 C57Bl/6 mice.

Figures 4A, 4B, 4C:
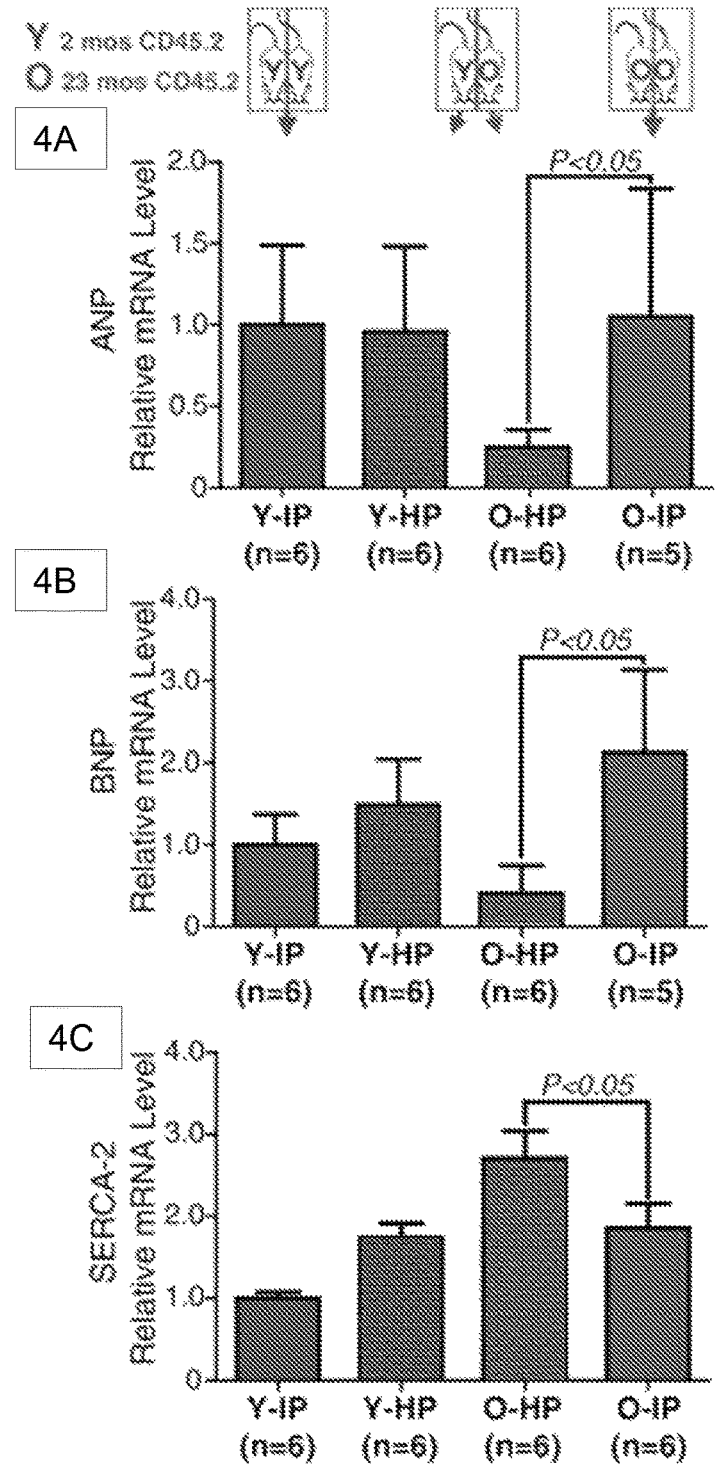
FIGS. 4A-4C depict molecular evidence for cardiac remodeling of aged myocardium by a young systemic circulation. RNA was extracted from hearts and analyzed by real-time PCR. ANP (FIG. 4A) and BNP (FIG. 4B) levels were significantly reduced in old mice exposed to a young circulation when compared to the old isochronic mice.

Heterochronic parabiosis is associated with molecular remodeling. Cardiac hypertrophy is associated with altered expression of a number of cardiac markers. To evaluate the reversal of hypertrophy in O-HP mice on a molecular level, the cardiac transcriptional expression of atrial natriuretic peptide (ANP) and brain natriuretic peptide (BNP), molecular markers of myocyte hypertrophy were quantified (FIGS. 4A-4B). A significant reduction in ANP and BNP transcript levels was detected in the hearts of old mice exposed to a young circulation, as compared to the isochronic age-matched controls. Transcript levels of sarcoplasmic reticulum calcium ATPase (SERCA-2), expression of which may vary with age (Dai et al., 2009) and is functionally important for normal diastolic relaxation was also quantified. SERCA-2 expression was significantly increased in hearts of aged mice exposed to a young circulation (O-HP) when compared to O-IP controls (FIG. 4C). These data provide additional evidence that young circulating factors modify discrete molecular pathways associated with cardiac myocyte hypertrophy and diastolic function.

Figure 11A:
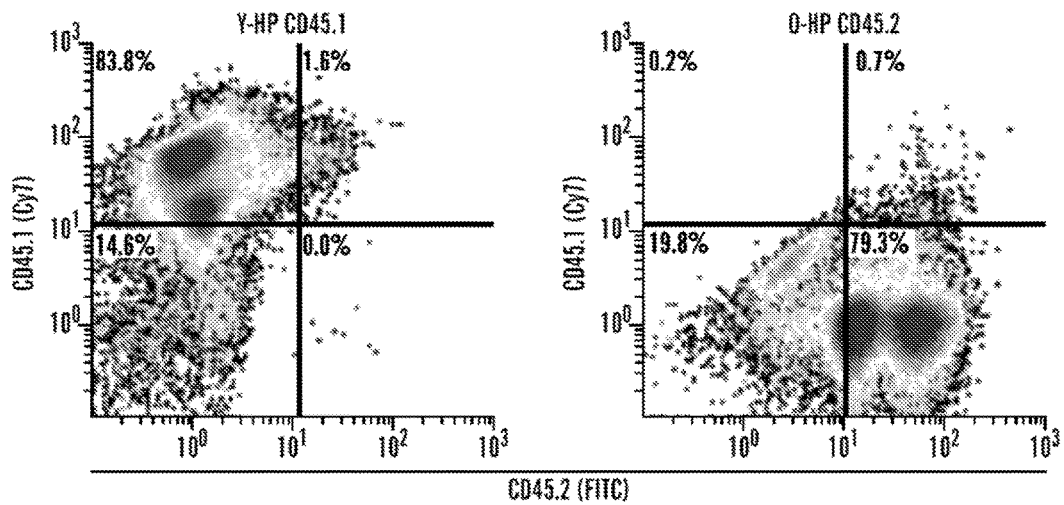
FIGS. 11A-11C demonstrate that heterochronic sham parabiosis does not reverse cardiac hypertrophy in aged mice.
Figure 11B:
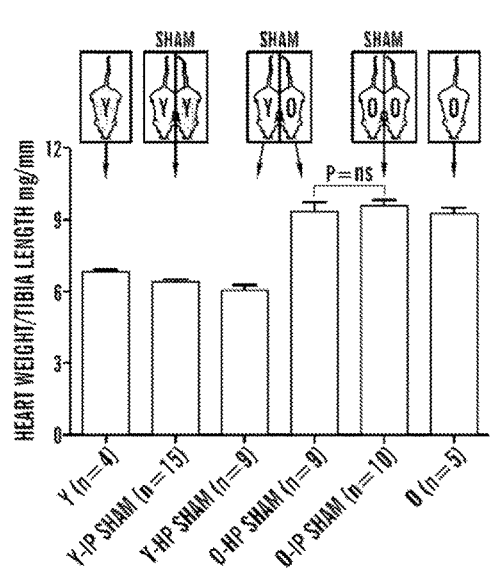
Figure 11C:
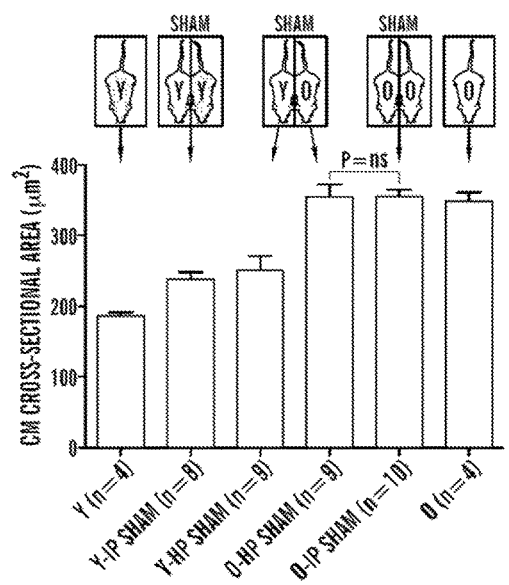

Behavioral changes associated with parabiosis do not explain reversal of cardiac hypertrophy in heterochronic mice. Although the parabiosis model has been used for physiological studies for over a century (Finerty, 1952), the possibility that the physical constraints of parabiotic pairing introduced behavioral changes that contributed to the observed reversal of cardiac hypertrophy was considered. Thus, a surgical technique described herein as "sham parabiosis" was developed, whereby mice are surgically joined while leaving the skin intact, such that they do not develop a shared circulation (FIG. 11A). Sham heterochronic parabiotic pairs, in which young female mice (2 months) were joined to aged partners (23 months) were generated and compared to sham isochronic parabiotic pairs (young—young or old—old) and to age-matched heterochronic and isochronic parabiotic pairs (FIG. 11A-11C). The hearts of sham pairs were analyzed after 4 wks, as in prior experiments. In contrast to conventional parabiotic joining, in which effective cross-circulation was established, no significant difference in heart weight to tibia length ratio was found in aged mice involved in sham heterochronic parabiosis, as compared to aged isochronic shams (9.38+/−0.39 vs. 9.63+/−0.22 mm/mg, P=ns) (FIG. 11B). These data indicate that cross-circulation and exchange of blood-borne factors is required for reversal of age-related cardiac hypertrophy. This finding was also confirmed at the cellular level, since cardiomyocyte size in aged heterochronic shams did not differ from myocyte size in aged isochronic shams (352.9±18.9 vs. 355.0±9.5 $\mu m^2$, P=ns) (FIG. 11C). Finally, ANP, BNP and SERCA-2 transcript levels were evaluated in sham operated pairs. Levels of these molecular markers of hypertrophy were either significantly increased (ANP) or unaltered (BNP and SERCA-2) in old heterochronic shams when compared to old isochronic shams (data not shown), indicating that the molecular remodeling associated with reduced cardiac hypertrophy does not occur in the absence of a shared circulation.

Figures 12A, 12B, 12C, 12D, 12E, 12F:
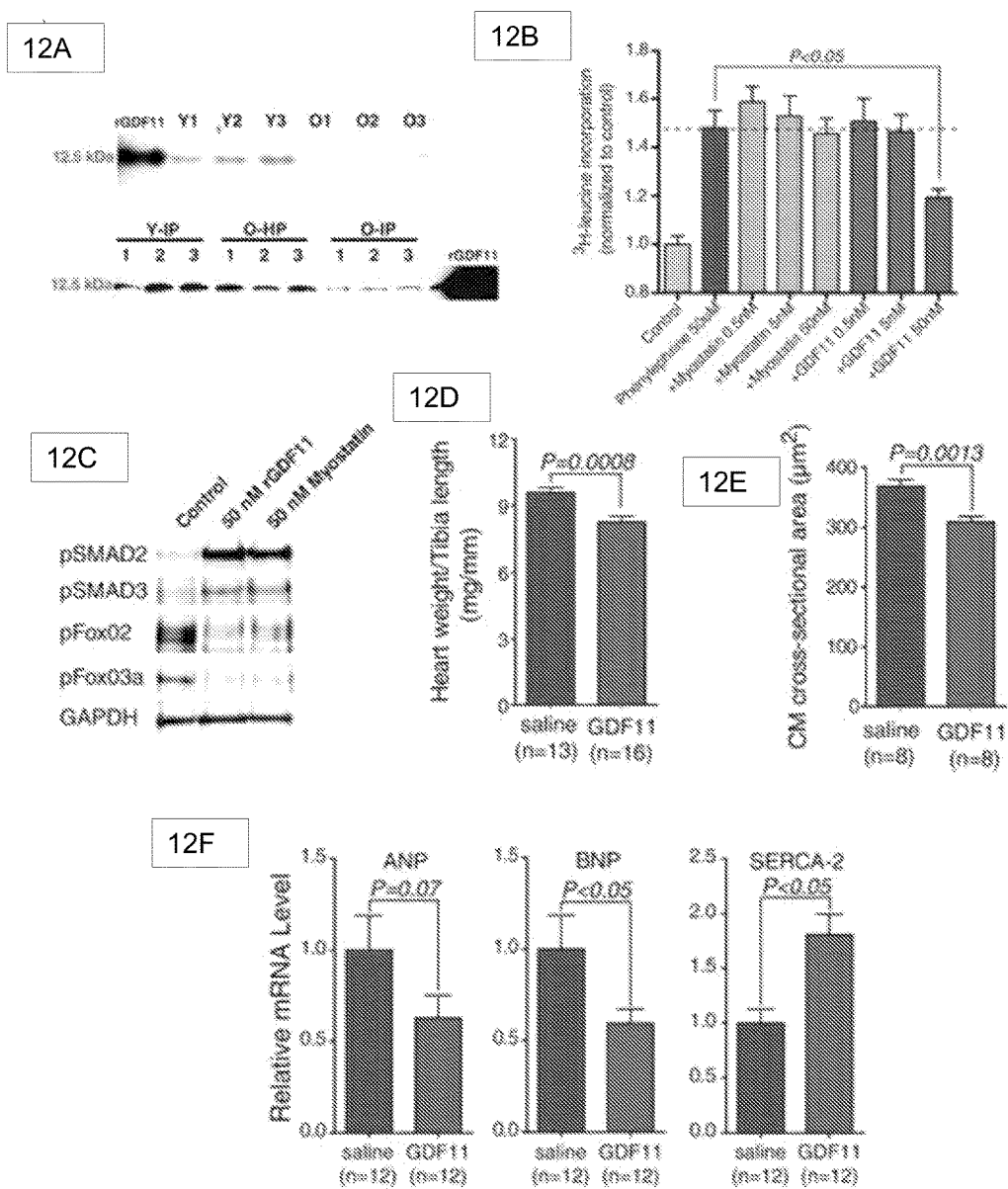
FIGS. 12A-12F demonstrate that circulating levels of GDF11 are reduced in aged mice and restoring GDF11 to "youthful" levels promotes reversal of cardiac hypertrophy and molecular remodeling.

Growth differentiation factor 11 is reduced in the circulation of aged mice and "Youthful" levels are restored by heterochronic parabiosis. The studies described above strongly suggest that differences in blood-borne factors in young versus old mice underlie the induced cardiac remodeling observed in old mice after heterochronic parabiosis. To identify candidates that might account for the regression of cardiac hypertrophy in old mice exposed to a youthful circulation, a series of screens on serum and plasma collected from young or old mice involved in isochronic or heterochronic parabiosis (4 weeks duration) were performed. With plasma from old parabionts exposed to a young circulation or from isochronic controls, we performed metabolomic profiling of 69 amino acids and amines; and lipidomics analysis, assessing 142 lipids from 9 lipid classes: lyso-phosphatidylcholines, lysophosphatidylethanolamines, sphingomyelins, phosphatidyl-cholines, diacylglycerols, cholesterol esters, phosphatidylethanolamines, phosphatidyl-inositols and triacylglycerols. However, no significant differences between heterochronic and isochronic parabiotic mice in either the metabolomic or the lipidomic screen were detected (data not shown). A broad scale proteomics analysis (SomaLogic, Inc. Boulder, Colo.) was next performed, using aptamer-based technology to quantitatively evaluate plasma samples from 10 young (2 month) and 10 old (23 month) mice. This approach revealed 13 analytes that reliably distinguished young mice from old mice (Table 1). Of these candidates, one (Growth differentiation factor 11, GDF11, a member of the activin/TGFβ superfamily of growth and differentiation factors) was confirmed in analyses of isochronic and heterochronic parabiotic mice to show differential abundance in the blood plasma of isochronic-old vs. isochronic-young pairs and a more "youthful" expression profile in old-heterochronic animals (FIG. 12A).

Figures 13A, 13B, 13C:
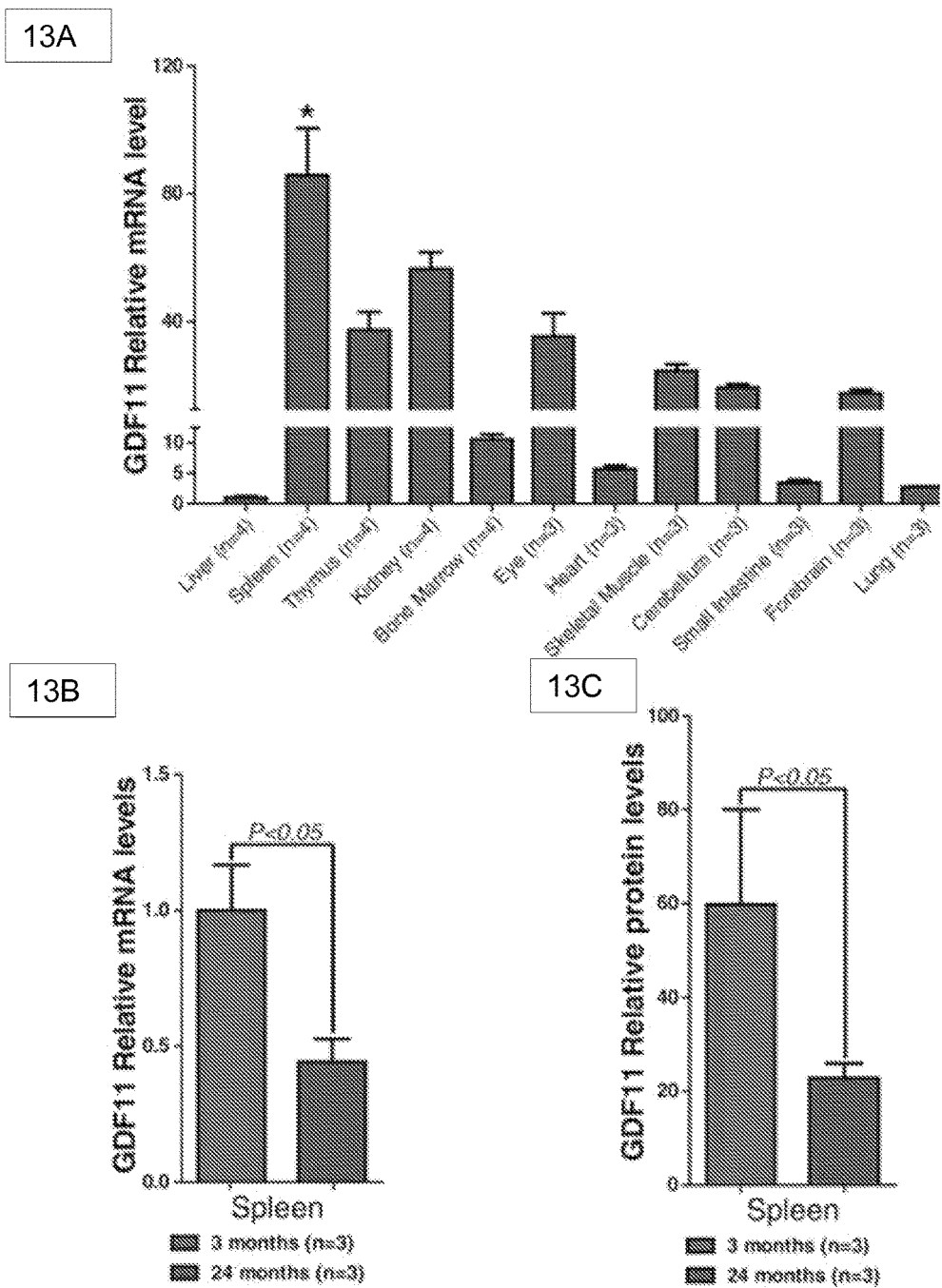
FIGS. 13A-13C demonstrate that spleen has a significantly higher level of GDF11 expression among the analyzed tissues and shows a significant age dependent reduction in GDF11 expression and protein synthesis.

To elucidate possible mechanisms for age dependent reduction in circulating GDF11, its expression was analyzed in a range of tissues and cell populations. The data suggest wide-spread expression, as previously reported (McPherron, 2010), with the spleen showing the highest levels of GDF11 mRNA (FIG. 13A). GDF11 expression was next examined as a function of age, comparing the tissues of old (24 months) and young (3 months) C57Bl/6 mice (FIGS. 13B-13C). A significant decline in both GDF11 gene expression and GDF11 protein levels was detected in the spleens of old mice. These data suggest that a reduction in splenic GDF11 could contribute to the decline of circulating GDF11 in aging mice, although as GDF11 is produced in many organs (McPherron, 2010), changes in expression in other tissues and organs may also contribute.

GDF11 prevents cardiac hypertrophy in vitro and suppresses forkhead transcription factor phosphorylation. It was next tested whether GDF11 displayed anti-hypertrophic properties in cultured neonatal cardiomyocytes using a leucine incorporation assay. After serum starvation, neonatal rat cardiomyocytes were treated for 24 h with recombinant GDF11 (rGDF11) or the closely related TGFβ superfamily protein myostatin at three different concentrations, followed by 24 h exposure to $^3$H-leucine and phenylephrine (50 μM). A significant and reproducible inhibition of phenylephrine-induced $^3$H-leucine incorporation was observed in myocytes treated with 50 nM rGDF11, an effect that was not observed after treatment with myostatin at the same concentration (FIG. 12B). The ability of rGDF11 or myostatin to activate TGFβ pathways was also tested in human induced pluripotent stem cell-derived cardiomyocytes, as previously shown in non-cardiac tissues (Tsuchida et al., 2008). Cells were stimulated for 15 min with serum free media (Control) or with the same media containing rGDF11 (50 nM) or Myostatin (50 nM). Cells stimulated with rGDF11 or with myostatin exhibited a significant increase in pSMAD2 and pSMAD3, consistent with activation of TGFβ pathway, and suppression of Forkhead transcription factor phosphorylation (FIG. 12C). Taken together, these data suggest that GDF11 has a direct anti-hypertrophic effect at the level of the cardiac myocyte.

Figure 14:
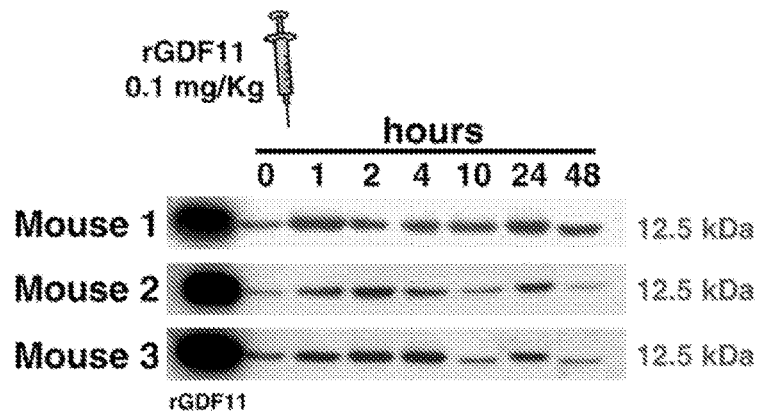
FIG. 14 demonstrates that GDF11 levels can be persistently increased for 24 hours in plasma after a single intraperitoneal bolus. GDF11 levels in plasma were evaluated by Western analysis at the indicated times after a single intraperitoneal injection of 0.1 mg/kg of recombinant GDF11 (n=3).

GDF11 reverses age related cardiac hypertrophy in vivo. Immunohistochemical staining of mouse cardiac sections with antibodies specific for GDF11 demonstrated evidence for GDF11 at the plasma membranes of cardiomyocytes, and specifically at the intercalated discs, supporting the concept that GDF11 has specific effects at the level of the cardiomyocyte (data not shown). Together with in vitro evidence (FIG. 12B-12C) supporting GDF11-mediated signaling in cardiomyocytes, these data provided the rationale to test whether restoring "youthful" levels of circulating GDF11 in aged mice might reverse age-related cardiac hypertrophy. To determine the optimal dosage, route and interval of administration of rGDF11, a dose-response study was performed, administering the protein to mice by bolus intraperitoneal (i.p.) injection at doses ranging from 0.005 to 0.1 mg/kg (data not shown). Only at the highest dose (0.1 mg/kg) was a reproducible increase in the plasma level of GDF11 1 h after injection observed (FIG. 14). Furthermore, analysis of plasma samples collected serially over 48 h after a single i.p. administration of 0.1 mg/kg rGDF11, indicated that GDF11 levels were persistently elevated for approximately 24 h after this single injection (FIG. 14).

Based on these results, a randomized, blinded, vehicle-controlled study to test the effects of rGDF11 on gross and histologic parameters of cardiac hypertrophy was designed. Old (23 month-old) female mice (C57Bl/6) received a daily intraperitoneal injection of rGDF11 (0.1 mg/kg) or saline for 30 days (n=16 per group). The heart weight to tibia length ratio was significantly lower in old mice injected with rGDF11 compared to the saline injected control group (FIG. 12D). Morphometric analysis further demonstrated that rGDF11 treatment resulted in significantly smaller cardiomyocytes compared to saline-injected controls (FIG. 12E).

Also investigated were the molecular changes in the hearts of rGDF11-treated aged mice. A significant reduction in BNP and a similar trend in ANP, both molecular markers associated with cardiac hypertrophy was detected (FIG. 12F). Conversely, SERCA-2 transcript levels, which correlate with diastolic function (Dai et al., 2009), were increased in rGDF11 treated hearts relative to saline-treated age-matched controls. This pattern of rGDF11-induced decrease in molecular markers of hypertrophy and increase in SERCA-2 expression resembles the pattern observed in old mice exposed to a young circulation by parabiosis. Echocardiographic evaluation of 24 month old male C56Bl/6 mice that were randomized to receive a daily intraperitoneal injection of rGDF11 (0.1 mg/Kg) or vehicle for 30 days was performed. None of the functional parameters we evaluated was significantly different between the two groups (Table 2).

Figures 15A, 15B, 15C:
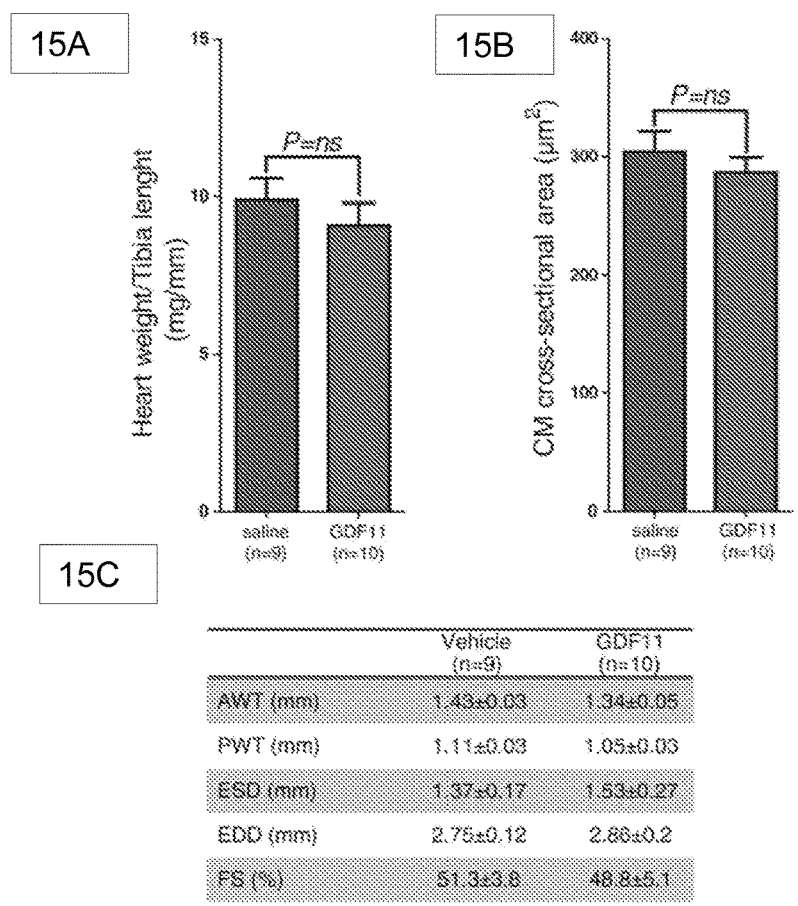
FIGS. 15A-15C demonstrate that supplementation of rGDF11 did not prevent development of cardiac hypertrophy after pressure overload by transverse aortic constriction in young mice.
Figure 16:
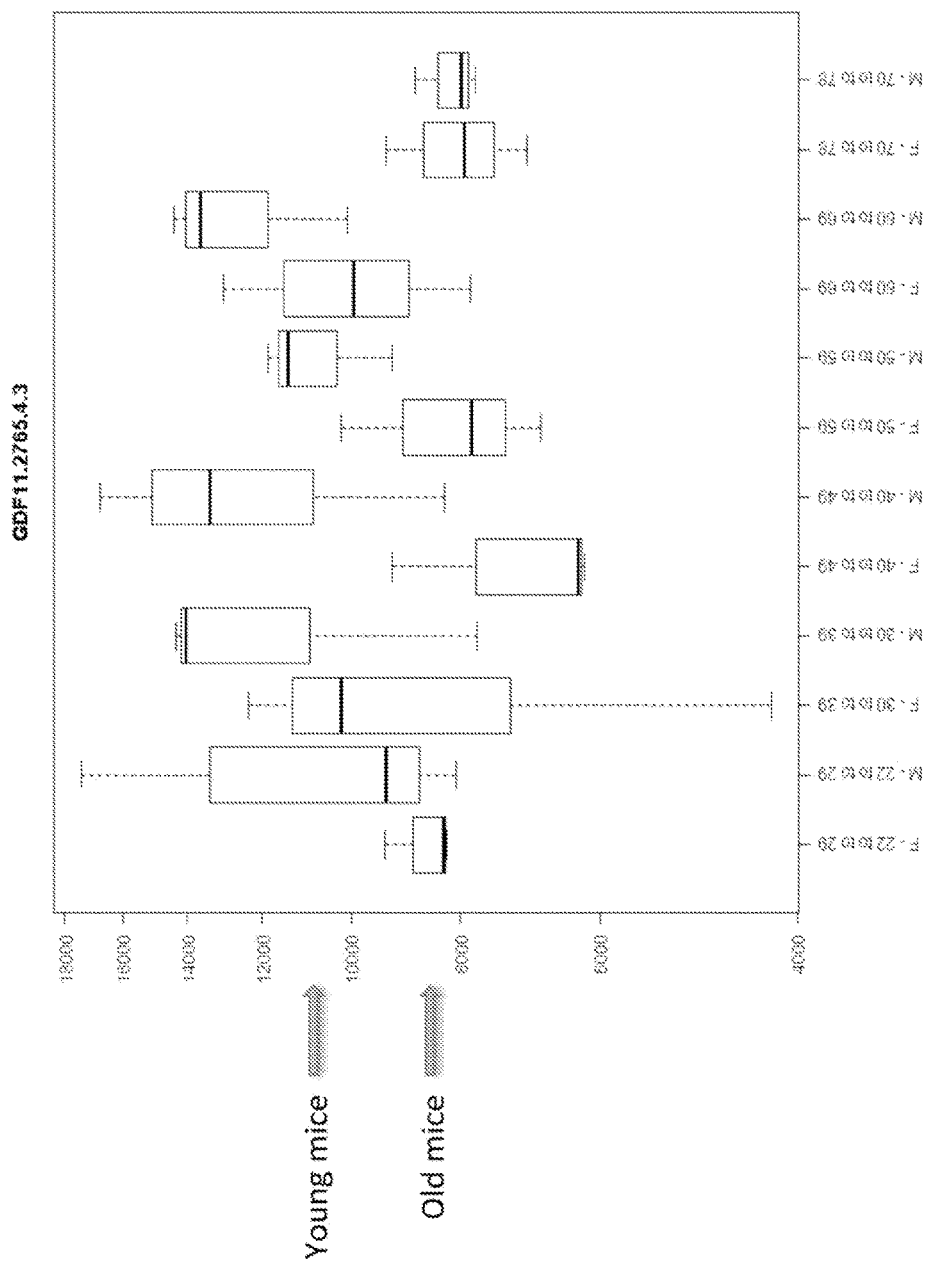
FIG. 16 depicts a graph of serum measurements of GDF11 protein in normal humans, n=3 per group, by age and gender. The approximate levels of young and old mice are shown to the left of the graph in arbitrary units.

GDF11 does not prevent cardiac hypertrophy after pressure overload in vivo. To determine if the effect of GDF11 on cardiomyocytes is specific for age-related cardiac hypertrophy, 2 month old female C56Bl/6 mice were subjected to transverse aortic constriction and then randomized to receive a daily IP injection of rGDF11 (0.1 mg/Kg) or vehicle for 30 days. An echocardiographic evaluation was performed at 15 days and then prior to sacrifice (FIG. 15C). After 30 days, mice were euthanized and hearts were collected for histological and molecular evaluation. Cardiac morphometry was evaluated by measuring the heart weight/tibia length ratio: there was no significant reduction in hypertrophy in mice subjected to aortic banding and treated for 30 days with rGDF11 (n=10) as compared with hearts of mice that received only vehicle (n=9) (P=0.4, FIG. 15A). Furthermore, cardiomyocyte cross sectional area was not significantly different (FIG. 15B). Development of cardiac fibrosis was evaluated and did not detect any difference between the two groups (data not shown). These data suggest that GDF11 does not prevent all forms of cardiac hypertrophy.

Discussion

Left ventricular hypertrophy is an important feature of cardiac aging, contributing to diastolic dysfunction and heart failure with preserved systolic function (Lakatta and Levy, 2003). An autopsy study of elderly subjects without hypertension or clinically evident cardiovascular disease performed by Anversa and colleagues describes cardiomyocyte enlargement and decreased cardiomyocyte number, without a change in total myocardial mass, a pattern that was more pronounced in males (Olivetti et al., 1995). A cross-sectional study of a similar patient population, however, suggests an increase in left ventricular wall thickness in both sexes (Lakatta and Levy, 2003). Patients with diastolic dysfunction tend to be older and are more likely to be obese, diabetic, hypertensive and female, compared to patients with systolic dysfunction (Owan and Redfield, 2005), suggesting distinct underlying pathological mechanisms.

The central hypothesis of this study is that the aging cardiac phenotype is reversible upon exposure to factors in a young circulation. This hypothesis was tested using surgically anastomosed parabiotic mice. C56Bl/6 mice were used for these experiments because they develop an age-related cardiac phenotype that resembles humans. In addition, because gender can play a role in physiologic cardiac hypertrophy (Foryst-Ludwig et al., 2011), experiments were performed in both males and females. Exposure of old mice to a young circulation via parabiosis reproducibly led to a reversal of cardiac myocyte hypertrophy in a gender-independent fashion, and this reduced cardiomyocyte size translated into a reduction in global cardiac mass. This structural transformation was accompanied by a reduction in myocardial gene expression of natriuretic peptides known to promote maladaptive cardiac remodeling and an increase in Ca2+ATPase (SERCA-2), the expression of which is integral to myocardial relaxation and hence normal diastolic function. Together, these data are consistent with the concept that factors present in a young circulation can reverse critical structural and molecular aspects of cardiac aging.

With circulatory transfer of a soluble substance emerging as a likely mechanism of cardiac hypertrophy regression in old parabiotic mice, a systematic search was performed to identify candidate factors present at higher levels in the blood of young mice that might underlie the anti-hypertrophic effect. The proteomic analysis identified several factors with levels that change with age, and it cannot be excluded that other factors also participate in the effect observed in heterochronic parabiosis; however, GDF11 emerged as a strong candidate from a series of screening analyses comparing the lipid profiles, metabolites, and signaling proteins present in young versus old plasma. While GDF11 expression is detectable in a range of tissues, the spleen shows the highest concentration, and exhibits an age dependent decline in GDF11 levels. Thus, the spleen may contribute to circulating GDF11 and an age-related production or secretory defect in the spleen could participate in the reduction in circulating GDF11 in old mice.

A recent study shows that the treatment of cachexic mice with soluble ActRIIB protein (sActRIIB), which antagonizes signaling by GDF11 (as well as myostatin, activin, and other TGFβ family members, given the promiscuity of the receptors (Tsuchida et al., 2008)) reverses cardiac atrophy in tumor-bearing animals (Zhou et al., 2010). Together with the proteomic data, this study further supported the notion that GDF11 acts as a mediator of the systemic anti-hypertrophic activity found in young mice. Moreover, the histological data (data not shown) suggested binding of GDF11 to cardiomyocytes in vivo. A randomized, vehicle-controlled study was therefore performed, administering rGDF11 to old mice for 30 d. This rGDF11 therapy led to a significant regression of cardiac hypertrophy in old mice, as indicated by both heart weight measurements and morphometric analyses.

Moreover, the demonstration that rGDF11, but not myostatin, induced a dose-dependent inhibition of phenylephrine-mediated hypertrophy in neonatal cardiac myocytes, in vitro, suggests that GDF11 has specific and direct effects at the level of the cardiac myocyte. Without wishing to be bound by theory, however, both rGDF11 and myostatin stimulated TGFβ signaling pathways in cardiomyocytes, suggesting that the activation of anti-hypertrophic FoxO factors may promote proteasome-mediated protein degradation (Sandri et al., 2004)

The observation that myostatin negatively regulates skeletal muscle mass led to the development of therapeutic strategies for age- and cancer-related muscle atrophy by blocking myostatin signaling. Interestingly, although myostatin null mice have not consistently demonstrated important changes in cardiac mass during aging (Cohn et al., 2007; Jackson et al., 2012), treatment with a soluble ActRIIB antagonist leads to increased skeletal and cardiac muscle mass, suggesting that the cardiac effects of this antagonist may arise from inhibition of a ligand other than myostatin. Indeed, despite signaling through similar activin receptor combinations, GDF11 and myostatin exhibit many non-overlapping functions. Myostatin null mice demonstrate substantially increased skeletal muscle mass, whereas GDF11 null mice exhibit skeletal and renal abnormalities and die within 24 h of birth (McPherron et al., 1999). Thus, it is contemplated therein that the reported ActRIIB antagonist effects on myocardium (Zhou et al., 2010) may be due to inhibition of GDF11 signaling and independent of effects on myostatin.

GDF11 was ineffective in preventing cardiac hypertrophy in the context of pressure overload. Interestingly, our preliminary studies suggest that GDF11 treatment may influence aging phenotypes in other tissues, such as skeletal muscle.

In summary, the analysis of reverse remodeling in the hearts of heterochronic parabiotic mice led to the identification of GDF11 as an age-regulated circulating factor with potent anti-hypertrophic properties. These studies implicate GDF11 in age-related cardiac hypertrophy (Table 1). Further, GDF11 does stimulate phosphorylation of target protein (SMAD2/3) in human pluripotent cell-derived cardiomyocytes (FIG. 12C). The results described herein provide therapeutic possibilities for targeting cardiac hypertrophy of aging by restoring youthful levels of circulating GDF11.

Experimental Procedures:

Animals. Aged (21-23 months) C57Bl/6 mice were obtained from the National Institute on Aging (NIA); young (2 months) C57Bl/6 (CD45.1$^-$CD45.2$^+$) or young B6.SJL (CD45.1$^+$CD45.2$^-$) mice were obtained from JAX.

Parabiosis. Parabiosis was performed as described previously (Bunster and Meyer, 1933; Ruckh et al., 2012). Blood chimerism was confirmed in a subset of parabiotic pairs by flow cytometry measuring the frequency of donor-derived blood cells from one partner (CD45.1$^+$) in the spleen of the other partner (CD45.2$^+$). Partner-derived cells typically represented 40-50% of splenocytes, consistent with establishment of parabiotic cross-circulation. Because old CD45.1+ mice are not commercially available we could not use this method to verify the establishment of chimerism in isochronic-old parabiotic pairs.

Sham Parabiosis. Sham parabiosis was performed as a modification of the parabiosis procedure (Bunster and Meyer, 1933; Ruckh et al., 2012) to achieve surgical joining without development of a shared circulation. Mice were anesthetized to full muscle relaxation and joined by a modification of the technique of Bunster and Meyer. After shaving the corresponding lateral aspects of each mouse, matching skin incisions were made from the olecranon to the knee joint of each mouse, and the subcutaneous fascia was bluntly dissected to create about ½ cm of free skin. The olecranon and knee joints were attached with a single 2-0 prolene suture. The suture was sequentially passed through the skin and joint of the first mouse, through a silicon disk to separate the skin of the two mice, and then through the skin and joint of the second mouse. The suture was tied, such that the silicon disk separated the skin of each mouse at the joint and without any contact between the cutaneous flaps of each mouse. The skin incisions were closed with staples. The prolene sutures connecting the mice were reinforced with meshed staples.

Morphometric Assessment of Cardiomyocyte Size. Mouse hearts were fixed with 4% paraformaldehyde, paraffin-embedded, sectioned, and stained with periodic acid Schiff (PAS). Staining, scanning, and quantification were carried out in a blinded manner using 5 randomly selected sections from the heart.

Noninvasive Blood Pressure. A computerized tail-cuff system (BP-2000, Visitech Systems, Apex, N.C.) was modified to allow simultaneous blood pressure measurement of both members of the parabiotic pair. Unoperated mice or pairs of mice were trained for 5 consecutive days in the pre-warmed tail-cuff device to accustom them to the procedure, followed by measurements of heart rate and systolic blood pressure.

Neurohormonal Measurements. Circulating levels of angiotensin II and aldosterone in serum samples were measured by ELISA (Enzo Life Sciences International, INC., USA)

Proteomic analysis. EDTA plasma samples (20 μl) from 20 mice were analyzed on the SomaLogic™ proteomics discovery platform (SOMAscan), which uses SOMAmers™ to measure 1001 proteins simultaneously. SOMAmers™ (Slow Off-rate Modified Aptamers) are nucleic acid-based protein binding reagents evolved through SELEX™ (Tuerk and Gold, 1990) to bind protein targets. SOMAscan™ transforms the concentration of proteins in the matrix into a relative quantity of SOMAmers™, through equilibration binding and removal of unbound SOMAmers™ and proteins. The SOMAmer™ quantity is measured by hybridization to microarrays (for a full description, see (Gold et al., 2010))

In vitro cardiac myocyte hypertrophy assay. Neonatal cardiac myocytes were isolated from post-natal day 1 CD1 rats (Charles River) (Seki et al., 2009). Approximately 36 h after plating, cardiac myocytes were serum starved for 24 h in low-glucose DMEM supplemented with ITS (PAA Laboratories). Cardiac myocytes were pretreated with myostatin (R&D Systems) or rGDF11 (Peprotech) for 24 h, prior to treating with phenylephrine (50 μM, Sigma) and assaying protein synthesis/hypertrophy with $^3$H-leucine (1 μCi/ml, Moravek). rGDF11 and myostatin treatments were continued during the period of exposure to phenylephrine and $^3$H-leucine. 24 h after labeling with $^3$H-leucine, cells were washed with ice-cold PBS and fixed with ice-cold 10% trichloroacetic acid for 45 min at 4 C. Cells were lysed with 0.05M NaOH and analyzed by liquid scintillation.

Statistical analyses. Data comparison subjected to one-way ANOVA and post-hoc Bonferonni correction or Student's t-test assuming two-tailed distribution and unequal variances. Statistical significance was assigned for $p<0.05$; results are shown as standard error of the mean.

Flow cytometry. All flow cytometry was performed on freshly isolated, unfixed splenocytes kept one ice during all incubation steps. Cells were blocked with HBSS/2% FBS for 10 min prior to resuspension at a concentration of $1\times10^6$ cells per 250 uL. Cells were incubated for 30 min in directly conjugated primary antibodies specific for CD45.1 (eBioscience) and CD45.2 (eBioscience) and washed twice in HBSS, prior to flow analysis. Conjugated isotype control antibodies were used in all experiments.

Gene expression analysis. To quantify expression genes commonly induced by hypertrophic stimuli, hearts from different experimental groups were excised and snap frozen in liquid nitrogen 4 weeks after surgery. RNA was extracted with Trizol reagent (Sigma), transcribed into cDNA with the High Capacity cDNA Reverse Transcription kit (Applied Biosystems) using random primers, and subsequently analyzed by real-time PCR on an Applied Biosystems 7300 Real Time PCR System using SYBR Green™ (Applied Biosystems) or TaqMan™ (Applied Biosystems) and primers for ANP (left: 5'-TCGTCTTGGCCTTTTGGCT-3' (SEQ ID NO: 4); right: 5'-TCCAGGTGGTCTAGCAGGTTCT-3' (SEQ ID NO: 5)), BNP (left: 5'-AGGGAGAACACGGCAT-CATT-3' (SEQ ID NO: 6); right: 5'-GACAGCACCTTCA-GGAGAT-3' (SEQ ID NO: 7)), SERCA-2 (left: 5'-TG-GAACAACCCGGTAAAGAGT-3' (SEQ ID NO: 13); right: 5'-CACCAGGGGCATAATGAGCAG-3'(SEQ ID NO: 14)), GDF1/(Mm01159973m1 TaqMan Gene Expression Assays, Life technologies). Results were normalized to expression of TATA binding protein and presented as fold increase relative to young isochronic animals based on the ΔΔCt method.

Metabolomic and lipidomic profiling analysis. LC-MS/MS analysis. Plasma metabolomic profiling was performed on a 4000 QTRAP triple quadrupole mass spectrometer (Applied Biosystems/Sciex, Foster City, Calif.) with a Turbo V electrospray source coupled to an HPLC system including an HTS PAL autosampler (Leap Technologies, Carrboro, N.C.) and a 1200 series binary pump (Agilent Technologies, Santa Clara, Calif.). This LC-MS/MS system was used for polar metabolites analysis employing hydrophilic-interaction liquid chromatography (HILIC) and also for lipid analysis, each requiring distinct methods of plasma extraction, LS/MS acquisition methods and instrument configurations. The MultiQuant software v. 2.0.2 (AB SCIEX, Foster City, Calif.) was used for automated peak integration and metabolite peaks also were manually reviewed for quality of integration (Roberts et al., 2012). HILIC: Hydrophilic-interaction liquid chromatography is suitable for analyzing hydrophilic metabolites; including amino acids, nucleotides and neurotransmitters. Ten microliters of plasma were extracted with 90 μL of 74.9:24.9:0.2 vol/vol/vol acetonitrile/methanol/formic acid containing 0.2 μg/mL (final concentration) of isotopically labeled valine-d8 and phenylalanine-d8 (Sigma-Aldrich; St Louis, Mo.). The samples were vortexed for 30 seconds, centrifuged (10 minutes, 10,000 rpm, 4° C.) and the supernatants were injected directly into the LC/MS system. Samples underwent hydrophilic interaction chromatography using a 150×2.1 mm Atlantis HILIC™ Silica column (Waters, Milford, Mass.): mobile-phase A, 10 mM ammonium formate and 0.1% formic acid;

and mobile-phase B, acetonitrile with 0.1% formic acid. The column was eluted isocratically with 5% mobile-phase A for 0.5 minutes followed by a linear gradient to 60% mobile-phase over 10 minutes and then back to 5% mobile-phase A for 17 minutes. Electrospray ionization (ESI) was used in positive multiple reaction monitoring (MRM) ion mode. Declustering potentials and collision energies were optimized for each metabolite by infusion of reference standards before sample analyses. The ion spray voltage was 5 kV, the source temperature was 425° C. and the MRM window was set to 70 msec. Formic acid, ammonium acetate, LC/MS grade solvents, and valine-d8 were obtained from Sigma-Aldrich (St. Louis, Mo.), with the remainder of isotopically-labeled analytical standards obtained from Cambridge Isotope Laboratories, Inc. (Andover, Mass.). The samples were run in a randomized order to minimize internal variation and were interspaced by mouse pooled plasma samples to account for temporal drift across all analyzed metabolites. The internal standard peak areas were monitored for quality control and individual samples with peak areas differing from the group mean by more than 2 standard deviations were reanalyzed. Metabolites analyzed were selected based on the following criteria: 1) known structural identity; 2) distribution across multiple biochemical pathways; 3) reliable measurement using LC/MS in a high throughput fashion; and, 4) low rate of missingness on our platform (<1%).

Lipid analysis: Ten microliters of plasma were extracted with 190 µl of isopropanol containing 0.25 µg/ml (final concentration) 1-dodecanoyl-2-tridecanoyl-sn-glycero-3-phosphocholine (Avanti Polar Lipids, Alabaster, Ala.). After centrifugation, supernatants were injected directly, followed by reverse-phase chromatography using a 150×3.0 mm Prosphere HP C4 column (Grace, Columbia, Md.): mobile-phase A, 95:5:0.1 vol/vol/vol 10 mM ammonium acetate/methanol/acetic acid; and mobile-phase B, 99.9:0.1 vol/vol methanol/acetic acid. The column was eluted isocratically with 80% mobile-phase A for 2 minutes followed by a linear gradient to 20% mobile-phase A over 1 minute, a linear gradient to 0% mobile phase A over 12 minutes, then 10 minutes at 0% mobile-phase A and a linear gradient to 80% mobile phase A over 9 minutes. MS analyses were carried out using electrospray ionization and Q1 scans in the positive ion mode. Ion spray voltage was 5.0 kV, the source temperature was 400° C. and the declustering potential was 70 V. For each lipid analyte, the first number denotes the total number of carbons in the lipid acyl chain(s) and the second number (after the colon) denotes the total number of double bonds in the lipid acyl chain(s).

Immunohistochemistry. Mouse hearts were fixed with 4% paraformaldehyde, paraffin embedded, sectioned, and stained with standard immunohistochemistry microscopy methods as previously described. An antigen retrieval step was used in all experiments, by heating samples in a citrate-based buffer (Dako) to 95° C. for 20 min. Primary antibodies were used as follows: rabbit GDF11 antibody 1:500 (Abcam) A biotinylated anti-rabbit secondary followed by ABC reagent and DAB (Vector Laboratories) were used for immunohistochemistry.

Induced pluripotent stem cell-derived human cardiomyocytes. Induced pluripotent stem cell-derived human cardiomyocytes (iPSC-CM) were obtained from Cellular Dynamics International (CDI) and cultured according to the manufacturer's instructions. Briefly, cells were plated at 580,000 viable cells per well in 5ug/ml fibronectin-coated 6 well plates in CDI Plating Medium. Medium was changed after 2 days to CDI Maintenance Medium, and 2 additional changes with this medium were performed at days 4 and 6 post-plating. At the latter point, cells were observed to be beating homogenously. At 7 days post-plating, medium was changed to serum-free DMEM (low glucose) and cells were incubated for an additional 24 h. At this time, cells were exposed to either control serum free media, or the same media with 50 nM myostatin (Peprotech) or 50 nM rGDF11 (Peprotech) for 15 mins Lysates were collected and western analyses were performed using standard methods. Antibodies used were from Cell Signaling Technology: phospho-Fox01/Fox03a (9464), phospho-SMAD2 (3108), phospho-SMAD3 (9520), GAPDH (2118).

Western blot analysis. Western blot analyses were performed as described previously (Seki et al., 2009). Membranes (polyvinylidene fluoride, PerkinElmer Life Sciences) were incubated with primary antibodies (anti-GDF11 diluted 1:1000, from Abcam) and detected with horseradish peroxidase-conjugated antibodies (1:2000, from Bio-Rad) and enhanced chemiluminescence (PerkinElmer Life Sciences). Spleen western blot analyses were performed with membranes (immune-Blot PVDF membrane, Bio-Rad) incubated with primary antibodies (anti-GDF11, Abcam, 1:500 dilution and alpha-tubuline, Sigma, 1:1000 dilution) and detected with IRDye conjugated antibodies (1:10000 dilution, Li-Cor). Membranes were scanned with Odyssey CLx Infrared Imaging System (Li-Cor) and quantified by densitometry with the Image Studio Software (Li-Cor).

Transverse aortic constriction and echocardiography. Transverse aortic constriction (TAC) surgery and Echocardiography were performed in in vivo studies using blinded protocols.

REFERENCES

Aurigemma, G. P. (2006). Diastolic heart failure—a common and lethal condition by any name. N Engl J Med 355, 308-310.

Balsam, L. B., Wagers, A. J., Christensen, J. L., Kofidis, T., Weissman, I. L., and Robbins, R. C. (2004). Haematopoietic stem cells adopt mature haematopoietic fates in ischaemic myocardium. Nature 428, 668-673.

Brack, A. S., Conboy, M. J., Roy, S., Lee, M., Kuo, C. J., Keller, C., and Rando, T. A. (2007). Increased Wnt signaling during aging alters muscle stem cell fate and increases fibrosis. Science 317, 807-810. Bunster, E., and Meyer, R. K. (1933). An improved method of parabiosis. The Anatomical Record 57, 339-343.

Cohn, R. D., Liang, H. Y., Shetty, R., Abraham, T., and Wagner, K. R. (2007). Myostatin does not regulate cardiac hypertrophy or fibrosis. Neuromuscul Disord 17, 290-296.

Conboy, I. M., Conboy, M. J., Wagers, A. J., Girma, E. R., Weissman, I. L., and Rando, T. A. (2005). Rejuvenation of aged progenitor cells by exposure to a young systemic environment. Nature 433, 760-764.

Dai, D. F., Santana, L. F., Vermulst, M., Tomazela, D. M., Emond, M. J., MacCoss, M. J., Gollahon, K., Martin, G. M., Loeb, L. A., Ladiges, W. C., et al. (2009). Overexpression of catalase targeted to mitochondria attenuates murine cardiac aging. Circulation 119, 2789-2797.

Eggan, K., Jurga, S., Gosden, R., Min, I. M., and Wagers, A. J. (2006). Ovulated oocytes in adult mice derive from non-circulating germ cells. Nature 441, 1109-1114.

Finerty, J. C. (1952). Parabiosis in physiological studies. Physiol Rev 32, 277-302.

Foryst-Ludwig, A., Kreissl, M. C., Sprang, C., Thalke, B., Bohm, C., Benz, V., Gurgen, D., Dragun, D., Schubert, C., Mai, K., et al. (2011). Sex differences in physiological cardiac hypertrophy are associated with exercise-mediated changes in energy substrate availability. Am J Physiol Heart Circ Physiol 301, H115-122.

Gold, L., Ayers, D., Bertino, J., Bock, C., Bock, A., Brody, E. N., Carter, J., Dalby, A. B., Eaton, B. E., Fitzwater, T., et al. (2010). Aptamer-based multiplexed proteomic technology for biomarker discovery. PLoS One 5, e15004.

Hunt, S. A., Abraham, W. T., Chin, M. H., Feldman, A. M., Francis, G. S., Ganiats, T. G., Jessup, M., Konstam, M. A., Mancini, D. M., Michl, K., et al. (2009). 2009 focused update incorporated into the ACC/AHA 2005 Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation. Circulation 119, e391-479.

Jackson, M. F., Luong, D., Vang, D. D., Garikipati, D. K., Stanton, J. B., Nelson, O. L., and Rodgers, B. D. (2012). The aging myostatin null phenotype: reduced adiposity, cardiac hypertrophy, enhanced cardiac stress response, and sexual dimorphism. J Endocrinol 213, 263-275.

Kitzman, D. W., and Daniel, K. R. (2007). Diastolic heart failure in the elderly. Clin Geriatr Med 23, 83-106.

Krege, J. H., Hodgin, J. B., Hagaman, J. R., and Smithies, 0. (1995). A noninvasive computerized tail-cuff system for measuring blood pressure in mice. Hypertension 25, 1111-1115.

Lakatta, E. G., and Levy, D. (2003). Arterial and cardiac aging: major shareholders in cardiovascular disease enterprises: Part II: the aging heart in health: links to heart disease. Circulation 107, 346-354. McPherron, A. C. (2010). Metabolic Functions of Myostatin and Gdf1 1 Immunol Endocr Metab Agents Med Chem 10, 217-231.

McPherron, A. C., Lawler, A. M., and Lee, S. J. (1999). Regulation of anterior/posterior patterning of the axial skeleton by growth/differentiation factor 11. Nat Genet 22, 260-264.

Olivetti, G., Giordano, G., Corradi, D., Melissari, M., Lagrasta, C., Gambert, S. R., and Anversa, P. (1995). Gender differences and aging: effects on the human heart. J Am Coll Cardiol 26, 1068-1079. Owan, T. E., and Redfield, M. M. (2005). Epidemiology of diastolic heart failure. Prog Cardiovasc Dis 47, 320-332.

Pietramaggiori, G., Scherer, S. S., Alperovich, M., Chen, B., Orgill, D. P., and Wagers, A. J. (2009). Improved cutaneous healing in diabetic mice exposed to healthy peripheral circulation. J Invest Dermatol 129, 2265-2274.

Ruckh, J. M., Zhao, J. W., Shadrach, J. L., van Wijngaarden, P., Rao, T. N., Wagers, A. J., and Franklin, R. J. (2012). Rejuvenation of regeneration in the aging central nervous system. Cell Stem Cell 10, 96-103.

Sandri, M., Sandri, C., Gilbert, A., Skurk, C., Calabria, E., Picard, A., Walsh, K., Schiaffino, S., Lecker, S. H., and Goldberg, A. L. (2004). Foxo transcription factors induce the atrophy-related ubiquitin ligase atrogin-1 and cause skeletal muscle atrophy. Cell 117, 399-412.

Schocken, D. D., Benjamin, E. J., Fonarow, G. C., Krumholz, H. M., Levy, D., Mensah, G. A., Narula, J., Shor, E. S., Young, J. B., and Hong, Y. (2008). Prevention of heart failure: a scientific statement from the American Heart Association Councils on Epidemiology and Prevention, Clinical Cardiology, Cardiovascular Nursing, and High Blood Pressure Research; Quality of Care and Outcomes Research Interdisciplinary Working Group; and Functional Genomics and Translational Biology Interdisciplinary Working Group. Circulation 117, 2544-2565.

Seki, K., Sanada, S., Kudinova, A. Y., Steinhauser, M. L., Handa, V., Gannon, J., and Lee, R. T. (2009). Interleukin-33 prevents apoptosis and improves survival after experimental myocardial infarction through ST2 signaling. Circ Heart Fail 2, 684-691.

Sherwood, R. I., Christensen, J. L., Conboy, I. M., Conboy, M. J., Rando, T. A., Weissman, I. L., and Wagers, A. J. (2004). Isolation of Adult Mouse Myogenic Progenitors; Functional Heterogeneity of Cells within and Engrafting Skeletal Muscle. Cell 119, 543-554.

Souza, T. A., Chen, X., Guo, Y., Sava, P., Zhang, J., Hill, J. J., Yaworsky, P. J., and Qiu, Y. (2008). Proteomic identification and functional validation of activins and bone morphogenetic protein 11 as candidate novel muscle mass regulators. Mol Endocrinol 22, 2689-2702.

Tsuchida, K., Nakatani, M., Uezumi, A., Murakami, T., and Cui, X. (2008). Signal transduction pathway through activin receptors as a therapeutic target of musculoskeletal diseases and cancer. Endocr J 55, 11-21.

Tuerk, C., and Gold, L. (1990). Systematic evolution of ligands by exponential enrichment: RNA ligands to bacteriophage T4 DNA polymerase. Science 249, 505-510.

Villeda, S. A., Luo, J., Mosher, K. I., Zou, B., Britschgi, M., Bieri, G., Stan, T. M., Fainberg, N., Ding, Z., Eggel, A., et al. (2011). The ageing systemic milieu negatively regulates neurogenesis and cognitive function. Nature 477, 90-94.

Wagers, A. J., Sherwood, R. I., Christensen, J. L., and Weissman, I. L. (2002). Little evidence for developmental plasticity of adult hematopoietic stem cells. Science 297, 2256-2259.

Wright, D. E., Wagers, A. J., Gulati, A. P., Johnson, F. L., and Weissman, I. L. (2001). Physiological migration of hematopoietic stem and progenitor cells. Science 294, 1933-1936.

Yin, F. C., Spurgeon, H. A., Rakusan, K., Weisfeldt, M. L., and Lakatta, E. G. (1982). Use of tibial length to quantify cardiac hypertrophy: application in the aging rat. Am J Physiol 243, H941-947.

Yoshioka, J., Imahashi, K., Gabel, S. A., Chutkow, W. A., Burds, A. A., Gannon, J., Schulze, P. C., MacGillivray, C., London, R. E., Murphy, E., et al. (2007). Targeted deletion of thioredoxin-interacting protein regulates cardiac dysfunction in response to pressure overload. Circ Res 101, 1328-1338.

Zhou, X., Wang, J. L., Lu, J., Song, Y., Kwak, K. S., Jiao, Q., Rosenfeld, R., Chen, Q., Boone, T., Simonet, W. S., et al. (2010). Reversal of cancer cachexia and muscle wasting by ActRIIB antagonism leads to prolonged survival. Cell 142, 531-543.

Roberts, L. D., Souza, A. L., Gerszten, R. E., and Clish, C. B. (2012). Targeted metabolomics. Curr Protoc Mol Biol Chapter 30, Unit 30 32 31-24.

Seki, K., Sanada, S., Kudinova, A. Y., Steinhauser, M. L., Handa, V., Gannon, J., and Lee, R. T. (2009). Interleukin-33 prevents apoptosis and improves survival after experimental myocardial infarction through ST2 signaling. Circ Heart Fail 2, 684-691.

TABLE 1

List of serum analytes identified by proteomic analysis.
The table summarizes the 13 analytes that
readily distinguish young mice from old mice.
Serum analytes
(SOMAscan)

Collectin kidney 1
Cathepsin D

TABLE 1-continued

List of serum analytes identified by proteomic analysis.
The table summarizes the 13 analytes that
readily distinguish young mice from old mice.
Serum analytes
(SOMAscan)

Dickkopf-related protein 4
Erythrocyte membrane protein 4.1|Protein 4.1R
Esterase D
Growth-differentiation factor 11|BMP-11
Hemoglobin
Interleukin-1 receptor accessory protein|IL-1 RAcP|IL1 R3
Natural killer group 2 member D|NKG2D
Ras-related C3 botulinum toxin substrate 1
GTP-binding nuclear protein Ran|ARA24
TIMP3|Tissue inhibitor of metalloproteinases 3
Thymidylate synthase

TABLE 2

Echocardiographic data after 30 days of treatment with rGDF11 or
vehicle in 23 months old C57Bl/6 male mice. No significant
differences were noted in echocardiographic parameters.
AWT = anterior wall thickness; PWT = posterior wall
thickness; EDD = end diastolic dimension; ESD = end
systolic dimension; FS = fractional shortening.
Data shown as mean ± S.E.M.

|         | Vehicle (n = 7) | GDF11 (n = 6)  |
|---------|-----------------|----------------|
| AWT (mm) | 1.39 ± 0.02    | 1.39 ± 0.01    |
| PWT (mm) | 1.10 ± 0.02    | 1.09 ± 0.04    |
| ESD (mm) | 1.25 ± 0.04    | 1.25 ± 0.03    |
| EDD (mm) | 2.99 ± 0.09    | 3.20 ± 0.05    |
| FS (%)   | 57.9 ± 1.6     | 60.9 ± 1.1     |

Example 2

GDF11

As described herein, cardiac hypertrophy of aging can be rapidly reversed in a matter of weeks by exposure to a young blood circulation. The data presented above herein suggest that there is a circulating factor that is transferred from the young mouse to the old mouse via the shared circulation that is responsible for the rapid regression of cardiac hypertrophy.

Figure 7A:
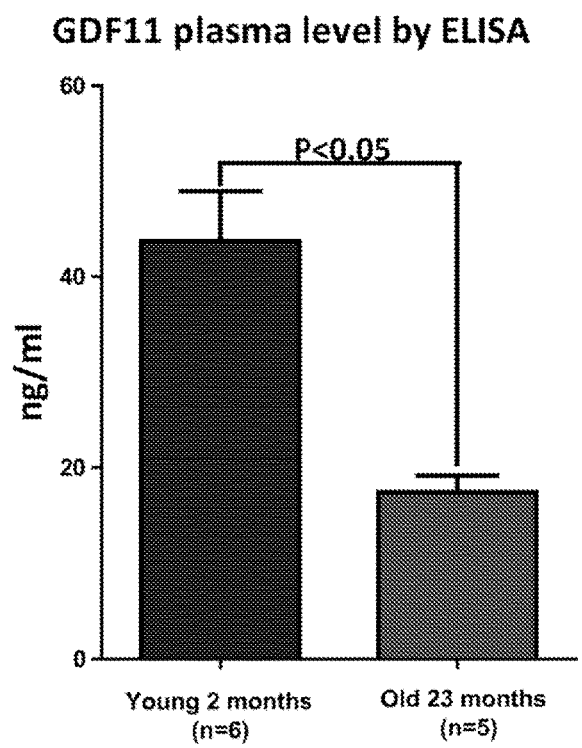
Figure 7B:
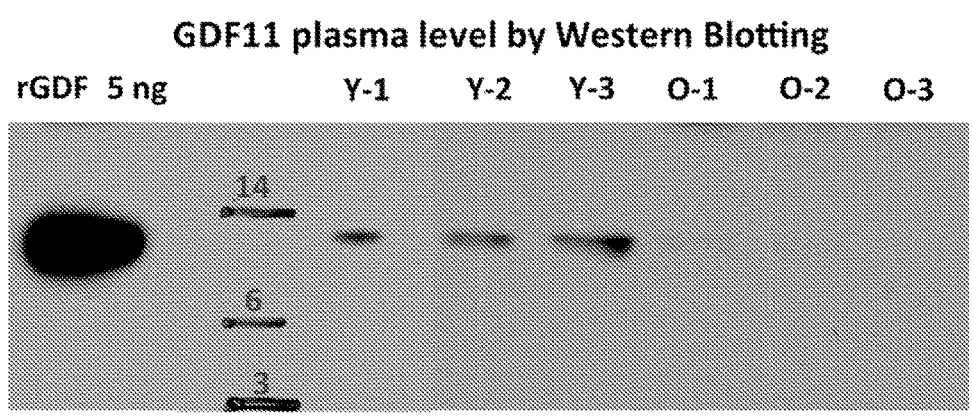
FIG. 7B depicts the results of a Western blot.

An unbiased search for circulating factors present in young mice that could account for the regression of cardiac hypertrophy observed in parabiotic mice was performed. Serum was collected from genetically identical mice from the two age-groups used in the parabiosis experiments, young adults and elderly mice. Using an aptamer-based proteomics platform (Somalogic), a factor called Growth differentiation factor (GDF) 11 was identified that was significantly reduced in old mice, compared to young mice. GDF11 plasma levels were measured by ELISA in Young (2 months) and Old mice (23 months). Circulating levels of GDF11 were significantly higher in young mice (43.7±12.7 ng/ml) when compared to old mice (17.4±3.9 ng/ml) (FIG. 7A). These results were confirmed by Western analysis on plasma from young (n=3) and old (n=3) mice. A 12.5 kDa band corresponding to the mature form of GDF11 is clearly visible in young mice and less intense in old mice (5 µl of plasma loaded in each lane)(FIG. 7B). Further, it was demonstrated that exposure of an old mouse to a young circulation resulted in the restoration of circulating GDF11 to levels similar to young mice (data not shown). From these data, a clear-cut inverse association emerges between circulating GDF11 and cardiac hypertrophy. Moreover, restoration of circulating GDF11 by parabiosis is associated with a regression in cardiac hypertrophy. These data indicate that a reduction in GDF11 with aging can play a role in age-related cardiac hypertrophy, and that an increase in GDF11 can prevent and/or reverse this hypertrophy.

The administration of active GDF11 can induce regression of cardiac hypertrophy and improve diastolic function and clinical heart failure. GDF11—with or without amino acid or other modifications aimed at reducing proteolytic degradation and prolonging half-life—can be used to treat cardiac hypertrophy and diastolic heart failure, including that associated with hypertension, aging, genetic hypertrophic cardiomyopathy, and valvular disease. A therapeutic strategy to restore youthful levels of GDF11 in patients with diastolic heart failure of any etiology is described herein.

REFERENCES

1. D. Lloyd-Jones et al., Circulation 121, e46 (Feb. 23, 2010).
2. F. Bursi et al., JAMA 296, 2209 (Nov. 8, 2006).
3. J. S. Gottdiener et al., Ann Intern Med 137, 631 (Oct. 15, 2002).
4. M. M. Redfield et al., JAMA 289, 194 (Jan. 8, 2003).
5. T. E. Owan et al., N Engl J Med 355, 251 (Jul. 20, 2006).
6. S. Stewart, K. MacIntyre, D. J. Hole, S. Capewell, J. J. McMurray, Eur J Heart Fail 3, 315 (June, 2001).
7. S. A. Hunt et al., Circulation 119, e391 (Apr. 14, 2009).
8. M. Ouzounian, D. S. Lee, P. P. Liu, Nat Clin Pract Cardiovasc Med 5, 375 (July, 2008).
9. J. C. Finerty, Physiol Rev 32, 277 (July, 1952).

Example 3

GDF11 can influence aging phenotypes in other tissues as well. These effects have been explored in several different tissues including skin, skeletal muscle, and brain.

In skeletal muscle GDF11 can reverse the age-related impairment of muscle stem cell genomic integrity, myogenic function and regenerative capacity.

Example 4

Serum levels of GDF11 protein in normal humans was determined using the apatmer technology described in Example 1. The levels in humans depend on gender but fall above the age of 70 in both men and women.

What is claimed herein:

1. A method of treating cardiac hypertrophy in a subject in need thereof, the method comprising administering to a subject a follistatin-GDF11 inhibitor, wherein the inhibitor is an inhibitory nucleic acid that directly reduces follistatin expression; whereby the level of GDF11 polypeptide in the subject is increased.

2. The method of claim 1, wherein the subject has or has been diagnosed with a condition selected from the group consisting of:
diastolic heart failure; cardiac hypertrophy; age-related cardiac hypertrophy; hypertension; valvular disease; aortic stenosis; genetic hypertrophic cardiomyopathy; or stiffness of the heart due to aging.

3. The method of claim 1, wherein in the level of GDF11 polypeptide is the level of free GDF11.

4. The method of claim 1, wherein the level of GDF11 polypeptide is the level of GDF11 in the circulation of the subject.

5. The method of claim 1, wherein the level of GDF11 polypeptide is the level of GDF11 in the cardiac tissue of the subject.

6. The method of claim 1, wherein the composition is administered via a route selected from the group consisting of:
intravenously; subcutaneously; intra-arterial; and intra-coronary arterial.

7. The method of claim 1, wherein the level of GDF11 is increased by at least 100%.

8. The method of claim 1, wherein the level of GDF11 is increased to at least 75% of a healthy reference level.

* * * * *

SEQUENCE LISTING

<160> NUMBER OF SEQ ID NOS: 17

<210> SEQ ID NO 1
<211> LENGTH: 407

<212> TYPE: PRT
<213> ORGANISM: Homo sapiens

<400> SEQUENCE: 1

Met Val Leu Ala Ala Pro Leu Leu Gly Phe Leu Leu Ala Leu
1               5                   10                  15

Glu Leu Arg Pro Arg Gly Glu Ala Glu Gly Pro Ala Ala Ala
            20                  25                  30

Ala Ala Ala Ala Ala Ala Ala Gly Val Gly Gly Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
                100                 105                 110

Ile Leu Asp Leu His Asp Phe Gln Gly Asp Ala Leu Gln Pro Glu Asp
            115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
            195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
        355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 2
<211> LENGTH: 383
<212> TYPE: PRT
<213> ORGANISM: Homo sapiens

<400> SEQUENCE: 2

Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
        35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
                85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125

Val Gln Thr Asp Gly Ser Pro Leu Cys Cys His Phe His Phe Ser Pro
    130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Gly Arg
            180                 185                 190

Arg His Ile Arg Ile Arg Ser Leu Lys Ile Glu Leu His Ser Arg Ser
        195                 200                 205

Gly His Trp Gln Ser Ile Asp Phe Lys Gln Val Leu His Ser Trp Phe
    210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
                245                 250                 255

Leu His Pro Phe Met Glu Leu Arg Val Leu Glu Asn Thr Lys Arg Ser
            260                 265                 270

Arg Arg Asn Leu Gly Leu Asp Cys Asp Glu His Ser Ser Glu Ser Arg
        275                 280                 285

Cys Cys Arg Tyr Pro Leu Thr Val Asp Phe Glu Ala Phe Gly Trp Asp
    290                 295                 300

Trp Ile Ile Ala Pro Lys Arg Tyr Lys Ala Asn Tyr Cys Ser Gly Gln
305                 310                 315                 320

Cys Glu Tyr Met Phe Met Gln Lys Tyr Pro His Thr His Leu Val Gln
                325                 330                 335

Gln Ala Asn Pro Arg Gly Ser Ala Gly Pro Cys Cys Thr Pro Thr Lys
            340                 345                 350

Met Ser Pro Ile Asn Met Leu Tyr Phe Asn Asp Lys Gln Gln Ile Ile

```
              355                 360                 365
Tyr Gly Lys Ile Pro Gly Met Val Val Asp Arg Cys Gly Cys Ser
    370                 375                 380

<210> SEQ ID NO 3
<211> LENGTH: 4260
<212> TYPE: DNA
<213> ORGANISM: Homo sapiens

<400> SEQUENCE: 3
tccccgcccc ccagtcctcc ctccccctccc ctccagcatg gtgctcgcgg cccgctgct       60 gctgggcttc ctgctcctcg ccctggagct gcggccccgg ggggaggcgg ccgagggccc      120
cgcggcggcg gcggcggcgg cggcggcggc ggcagcggcg ggggtcgggg gggagcgctc      180
cagccggcca gccccgtccg tggcgcccga gccggacggc tgccccgtgt gcgtttggcg      240
gcagcacagc cgcgagctgc gcctagagag catcaagtcg cagatcttga gcaaactgcg      300
gctcaaggag gcgcccaaca tcagccgcga ggtggtgaag cagctgctgc caaggcgcc       360 gccgctgcag cagatcctgg acctacacga cttccagggc gacgcgctgc agcccgagga      420
cttcctggag gaggacgagt accacgccac caccgagacc gtcattagca tggcccagga      480
gacggaccca gcagtacaga cagatggcag ccctctctgc tgccattttc acttcagccc      540
caaggtgatg ttcacaaagg tactgaaggc ccagctgtgg gtgtacctac ggcctgtacc      600
ccgcccagcc acagtctacc tgcagatctt gcgactaaaa cccctaactg gggaagggac      660
cgcaggggga gggggcggag gccggcgtca catccgtatc cgctcactga agattgagct      720
gcactcacgc tcaggccatt ggcagagcat cgacttcaag caagtgctac acagctggtt      780
ccgccagcca cagagcaact ggggcatcga gatcaacgcc tttgatccca gtggcacaga      840
cctggctgtc acctccctgg ggcgggagc cgaggggctg catccattca tggagcttcg      900
agtcctagag aacacaaaac gttcccggcg gaacctgggt ctggactgcg acgagcactc      960
aagcgagtcc cgctgctgcc gatatcccct cacagtggac tttgaggctt cggctgggga     1020
ctggatcatc gcacctaagc gctacaaggc caactactgc tccggccagt gcagtacat      1080 gttcatgcaa aaatatccgc atacccattt ggtgcagcag gccaatccaa gaggctctgc     1140 tgggcccctgt tgtaccccca ccaagatgtc cccaatcaac atgctctact tcaatgacaa     1200
gcagcagatt atctacggca gatccctgg catggtggtg gatcgctgtg ctgctctta       1260 aggtggggga tagaggatgc ctcccccaca gaccctaccc caagacccct agccctgccc     1320
ccatcccccc aagccctaga gctccctcca ctcttcccgc gaacatcaca ccgttccccg     1380
accaagccgt gtgcaataca acagagggag gcaggtggga attgagggtg aggggtttgg     1440
gggaaagggg aagcagggc atagtcaggg tggggagtgt ttgaagtttg cagatgagaa     1500
ggtttgacaa aaagacagag agatgtagag acagtgatag acagagga acaaaaagag      1560 cagcagtgag aaggcaaaga gagaggcaga agagacagac gaggcagaga caaaacactg     1620
agaaagagac tgaaatggag taataaatga aagccccaca ccaagcctcc tttcttccac     1680
tggcaaggtg aggggcttgg tatagtttgg ggagatcccc tgactattca gtaggagaag     1740
aaatcaaaaa tccattcttt tctccttctc tccctccaac agtggccagg ggaagggaa      1800 gtgagggcag gggcaaaaag atttgggaat tttatttat ttatttattg tgacttttca     1860
tttttttggt atttggcttt actggaatag gagggcccct gcccactgtg cccgttttat     1920
cccttattcc ccaaaccctg ctctccccaa cacctactca cttaagcact tgtataaagc     1980
```

```
ctccagggtt gggaatggga gtaaagggca agagggcgga cacatgaagt ttagtttcta    2040
acccatcatc accctaactc aacctttcct gagccaaatg gcttgaattg aagccagttg    2100
tcatggaaat agtaagaggt tagggtttaa gagctgggga tgcgggggtg ggagagagaa    2160
ccctcaacat ccaggatcta taatgaga gctactttaa accctcaggt ccaccctcat      2220
gatgctgagt tatttagcca gagggtgcag cctgcttatg cccaaattcc ctcagccaag    2280
agagagacca aagagcctct ggaatggccc tgctcccagc ctctatcttc aggtcaatta    2340
gagagagtat agagaccccca gagtcccctg ggtctggaaa gcgttaggag aggtcaagaa   2400
aggagcagta aggaggctga aggttacagg gcatttgaat ccaaatcact gctctgggct    2460
agggaataga gccagcagac caaggtggga aggattctgg aaggggggaca ttttagtctc   2520 ctaaccccaa agctcaggt ggaagagggg agaacaagga agcagagtgt ataattattt     2580
tttcctttta tttttggaat ctaacagtac ctggcagcag ggaggggaaa gtacagtggg    2640
gaaaagcatc tgacaaggcc agttagaaca gaggatggga aggatggaga ctcccgggct    2700
tggaaggcta ggaagcaggc agagactggt tgccatttca agtcactagc taggcccatt    2760
cattcctccc acaaccctga cccattctcc tctggactca ctgtgcctca gtttcttccc    2820
ctcaatggaa tgagaaatga cagcacccgc cacagccaag agatgaattc tgagcactta   2880
ccacgggcac tttatggaca taaaatacct ctcgctgtgg gacagataac cagggcacca   2940
gagtagtggt gaagagatgt gaggcttaag aggagtcaca ggcttcagag tacaagttcc   3000
cctctgcctc ccagctggac agtgcctaga agccaaggag ttgagaatct cctgatccac   3060 acccctatcct tacttcacca ccaggcctct ggctccagg caagagctta gggatgtca   3120 ggagaggtgg gggtaagaat cttcagcaaa actgtcactc taagtagagc cagcagttac   3180
gggtctgata aaacagtac tgaactaaag taaagcccaa gctggtgagc aaaactggat    3240
ggctcattct tcccaagagc atgactctcc cccttggcca gttggtggaa ggggcaaagg   3300
tatgtgacca cccttgagaa ggtgatgttg gtgagctta acatcttatt cctattctta    3360
tagtgagaaa gtgaaacaag atcttcagt agaggaatgg gcagggctgt taggctcttc    3420
agcttgcctt cacccatata gcagctatgc taaccccaag cctctctggc cctgttcttc   3480
atccttcctt ctgccccaat cctgaaggac aagacacacc cggccatcaa caccactcac   3540
atttccttgg tggaaggaaa ggaacagaga agtgaagaac agatacctcc ctccaaggtc   3600
aaatgcctcg tgatcttggc agagtaggga ttgggcaata agcatcaggt atcttccctc   3660
tacagattct agagagctgg ggcattaaat atgggggaca cttagaatac agctccttaa   3720
ataccaccaa ataaagacct tgtgtgtgt gtggtgggtg ggggggggggc aggggtcttt   3780 ctcttatgaa cataaatctg tgagctgaag tctcattccc ctgttcctcc ctaccccaa    3840 agaggcacag agtgaaggga cttgggggggc acagctcagc aacccagtgg gagttagcac   3900
cccctcccac cttatgatgt gtgtggacct ggccagtgcc cctctgaaca tatcattatt    3960
agtgtaatta tcatttattt tgtgtatttg tcacattgtg tgcatgacag cctttgttaa   4020
gggtgtctga ggagtatgga gctgacaggg gcattggaat gccaggaaag aacttcttca   4080
actgagatca aggcttcctg gagggaacca ctgcaaaaag gccatcaggc agttttcaag   4140
ttatgtgaca gagggcaaag acggccatag ggtgctctga gttttgggat ggtcacatga   4200
cacaatccag cacttgaacc tgaaaaaaaa aataaaagcg gtcaaagagt ttagaattca   4260
```

<210> SEQ ID NO 4
<211> LENGTH: 19

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcgtcttggc cttttggct                                                    19

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tccaggtggt ctagcaggtt ct                                                22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agggagaaca cggcatcatt                                                   20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacagcacct tcaggagat                                                    19

<210> SEQ ID NO 8
<211> LENGTH: 109
<212> TYPE: PRT
<213> ORGANISM: Homo sapiens

<400> SEQUENCE: 8

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Gln Cys Glu
            35                  40                  45

Tyr Met Phe Met Gln Lys Tyr Pro His Thr His Leu Val Gln Gln Ala
        50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
                100                 105

<210> SEQ ID NO 9
<211> LENGTH: 274
<212> TYPE: PRT
<213> ORGANISM: Homo sapiens

<400> SEQUENCE: 9

Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
        35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
                85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125

Val Gln Thr Asp Gly Ser Pro Leu Cys Cys His Phe His Phe Ser Pro
    130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Gly Arg
            180                 185                 190

Arg His Ile Arg Ile Arg Ser Leu Lys Ile Glu Leu His Ser Arg Ser
        195                 200                 205

Gly His Trp Gln Ser Ile Asp Phe Lys Gln Val Leu His Ser Trp Phe
    210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
                245                 250                 255

Leu His Pro Phe Met Glu Leu Arg Val Leu Glu Asn Thr Lys Arg Ser
            260                 265                 270

Arg Arg

<210> SEQ ID NO 10
<211> LENGTH: 2525
<212> TYPE: DNA
<213> ORGANISM: Homo sapiens

<400> SEQUENCE: 10
gggaagtcgg tgccgctgcc gtctctgcgt tcgccatgcg tcccggggcg ccagggccac      60
tctggcctct gccctggggg gccctggctt gggccgtggg cttcgtgagc tccatgggct     120
cggggaaccc cgcgcccggt ggtgtttgct ggctccagca gggccaggag ccacctgca      180 gcctggtgct ccagactgat gtcacccggg ccgagtgctg tgcctccggc aacattgaca     240
ccgcctggtc aacctcacc cacccgggga acaagatcaa cctcctcggc ttcttgggcc      300
ttgtccactg ccttccctgc aaagattcgt gcgacggcgt ggagtgcggc ccgggcaagg     360

```
cgtgccgcat gctgggggc cgcccgcgct gcgagtgcgc gcccgactgc tcggggctcc    420
cggcgcggct gcaggtctgc ggctcagacg gcgccaccta ccgcgacgag tgcgagctgc    480
gcgccgcgcg ctgccgcggc cacccggacc tgagcgtcat gtaccggggc cgctgccgca    540
agtcctgtga gcacgtggtg tgcccgcggc cacagtcgtg cgtcgtggac cagacgggca    600
gcgcccactg cgtggtgtgt cgagcggcgc cctgccctgt gcctccagc cccggccagg     660
agctttgcgg caacaacaac gtcacctaca tctcctcgtg ccacatgcgc caggccacct    720
gcttcctggg ccgctccatc ggcgtgcgcc acgcgggcag ctgcgcaggc acccctgagg    780
agccgccagg tggtgagtct gcagaagagg aagagaactt cgtgtgagcc tgcaggacag    840
gcctgggcct ggtgcccgag gcccccatc atccctgtt atttattgcc acagcagagt      900
ctaatttata tgccacggac actccttaga gcccggattc ggaccacttg gggatcccag    960
aacctccctg acgatatcct ggaaggactg aggaagggag gcctggggc cggctggtgg    1020
gtgggataga cctgcgttcc ggacactgag cgcctgattt agggccttc tctaggatgc    1080
cccagcccct accctaagac ctattgccgg ggaggattcc acacttccgc tcctttgggg   1140
ataaacctat taattattgc tactatcaag agggctgggc attctctgct ggtaattcct   1200
gaagaggcat gactgctttt ctcagcccca agcctctagt ctgggtgtgt acggagggtc   1260
tagcctgggt gtgtacggag ggtctagcct gggtgagtac ggagggtcta gcctgggtga   1320
gtacggaggg tctagcctgg gtgagtacgg agggtctagc ctgggtgtgt atggaggatc   1380
tagcctgggt gagtatggag ggtctagcct gggtgagtat ggagggtcta gcctgggtgt   1440
gtatggaggg tctagcctgg gtgagtatgg agggtctagc ctgggtgtgt atggagggtc   1500
tagcctgggt gagtatggag ggtctagcct gggtgtgtac ggagggtcta gtctgagtgc   1560
gtgtggggac ctcagaacac tgtgaccta gcccagcaag ccaggccctt catgaaggcc   1620
aagaaggctg ccaccattcc ctgccagccc aagaactcca gcttcccac tgcctctgtg   1680
tgcccctttg cgtcctgtga aggccattga gaaatgccca gtgtgccccc tgggaaaggg   1740
cacggcctgt gctcctgaca cgggctgtgc ttggccacag aaccacccag cgtctcccct   1800
gctgctgtcc acgtcagttc atgaggcaac gtcgcgtggt ctcagacgtg gagcagccag   1860
cggcagctca gagcagggca ctgtgtccgg cggagccaag tccactctgg gggagctctg   1920
gcggggacca cgggccactg ctcacccact ggccccgagg ggggtgtaga cgccaagact   1980
cacgcatgtg tgacatccgg agtcctggag ccgggtgtcc cagtggcacc actaggtgcc   2040
tgctgcctcc acagtgggt tcacacccag ggctccttgg tccccacaa cctgccccgg    2100
ccaggcctgc agaccagac tccagccaga cctgcctcac ccaccaatgc agccggggct    2160
ggcgacacca gccaggtgct ggtcttgggc cagttctccc acgacggctc accctcccct   2220
ccatctgcgt tgatgctcag aatcgcctac ctgtgcctgc gtgtaaacca cagcctcaga   2280
ccagctatgg ggagaggaca acacggagga tatccagctt ccccggtctg gggtgaggaa   2340
tgtggggagc ttgggcatcc tcctccagcc tcctccagcc cccaggcagt gccttacctg   2400
tggtgcccag aaaagtgccc ctaggttggt gggtctacag gagcctcagc caggcagccc   2460
accccaccct ggggccctgc ctcaccaagg aaataaagac tcaagccatt taaaaaaaaa   2520
aaaaa                                                              2525
```

<210> SEQ ID NO 11
<211> LENGTH: 263
<212> TYPE: PRT

<213> ORGANISM: Homo sapiens

<400> SEQUENCE: 11

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Gly Gly Glu Ser Ala
                245                 250                 255

Glu Glu Glu Glu Asn Phe Val
            260

<210> SEQ ID NO 12
<211> LENGTH: 337
<212> TYPE: PRT
<213> ORGANISM: Homo sapiens

<400> SEQUENCE: 12

Cys Asn Ala Cys Thr Trp Arg Gln Asn Thr Lys Ser Ser Arg Ile Glu
1               5                   10                  15

Ala Ile Lys Ile Gln Ile Leu Ser Lys Leu Arg Leu Glu Thr Ala Pro
            20                  25                  30

Asn Ile Ser Lys Asp Val Ile Arg Gln Leu Leu Pro Lys Ala Pro Pro
        35                  40                  45

Leu Arg Glu Leu Ile Asp Gln Tyr Asp Val Gln Arg Asp Asp Ser Ser
    50                  55                  60

Asp Gly Ser Leu Glu Asp Asp Tyr His Ala Thr Thr Glu Thr Ile
65                  70                  75                  80

Ile Thr Met Pro Thr Glu Ser Asp Phe Leu Met Gln Val Asp Gly Lys

```
                85                  90                  95
Pro Lys Cys Cys Phe Lys Phe Ser Ser Lys Ile Gln Tyr Asn Lys
            100                 105                 110
Val Val Lys Ala Gln Leu Trp Ile Tyr Leu Arg Pro Val Glu Thr Pro
            115                 120                 125
Thr Thr Val Phe Val Gln Ile Leu Arg Leu Ile Lys Pro Met Lys Asp
    130                 135                 140
Gly Thr Arg Tyr Thr Gly Ile Arg Ser Leu Lys Leu Asp Met Asn Pro
145                 150                 155                 160
Gly Thr Gly Ile Trp Gln Ser Ile Asp Val Lys Thr Val Leu Gln Asn
                165                 170                 175
Trp Leu Lys Gln Pro Glu Ser Asn Leu Gly Ile Glu Ile Lys Ala Leu
            180                 185                 190
Asp Glu Asn Gly His Asp Leu Ala Val Thr Phe Pro Gly Pro Gly Glu
            195                 200                 205
Asp Gly Leu Asn Pro Phe Leu Glu Val Lys Val Thr Asp Thr Pro Lys
    210                 215                 220
Arg Ser Arg Arg Asp Phe Gly Leu Asp Cys Asp Glu His Ser Thr Glu
225                 230                 235                 240
Ser Arg Cys Cys Arg Tyr Pro Leu Thr Val Asp Phe Glu Ala Phe Gly
                245                 250                 255
Trp Asp Trp Ile Ile Ala Pro Lys Arg Tyr Lys Ala Asn Tyr Cys Ser
            260                 265                 270
Gly Glu Cys Glu Phe Val Phe Leu Gln Lys Tyr Pro His Thr His Leu
            275                 280                 285
Val His Gln Ala Asn Pro Arg Gly Ser Ala Gly Pro Cys Cys Thr Pro
    290                 295                 300
Thr Lys Met Ser Pro Ile Asn Met Leu Tyr Phe Asn Gly Lys Glu Gln
305                 310                 315                 320
Ile Ile Tyr Gly Lys Ile Pro Ala Met Val Val Asp Arg Cys Gly Cys
                325                 330                 335
Ser

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggaacaacc cggtaaagag t                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccaggggc ataatgagca g                                           21

<210> SEQ ID NO 15
<211> LENGTH: 15
<212> TYPE: PRT
```

-continued

<213> ORGANISM: Homo sapiens

<400> SEQUENCE: 15

Asn Met Leu Tyr Phe Asn Asp Lys Gln Gln Ile Ile Tyr Gly Lys
1               5                   10                  15

<210> SEQ ID NO 16
<211> LENGTH: 15
<212> TYPE: PRT
<213> ORGANISM: Homo sapiens

<400> SEQUENCE: 16

Ser Gly Gln Cys Glu Tyr Met Phe Met Gln Lys Tyr Pro His Thr
1               5                   10                  15

<210> SEQ ID NO 17
<211> LENGTH: 361
<212> TYPE: PRT
<213> ORGANISM: Mus musculus

<400> SEQUENCE: 17

Arg Ser Ser Arg Pro Ala Pro Ser Ala Pro Pro Glu Pro Asp Gly Cys
1               5                   10                  15

Pro Val Cys Val Trp Arg Gln His Ser Arg Glu Leu Arg Leu Glu Ser
                20                  25                  30

Ile Lys Ser Gln Ile Leu Ser Lys Leu Arg Leu Lys Glu Ala Pro Asn
            35                  40                  45

Ile Ser Arg Glu Val Val Lys Gln Leu Leu Pro Lys Ala Pro Pro Leu
        50                  55                  60

Gln Gln Ile Leu Asp Leu His Asp Phe Gln Gly Asp Ala Leu Gln Pro
65                  70                  75                  80

Glu Asp Phe Leu Glu Glu Asp Glu Tyr His Ala Thr Thr Glu Thr Val
                85                  90                  95

Ile Ser Met Ala Gln Glu Thr Asp Pro Ala Val Gln Thr Asp Gly Ser
            100                 105                 110

Pro Leu Cys Cys His Phe His Phe Ser Pro Lys Val Met Phe Thr Lys
        115                 120                 125

Val Leu Lys Ala Gln Leu Trp Val Tyr Leu Arg Pro Val Pro Arg Pro
130                 135                 140

Ala Thr Val Tyr Leu Gln Ile Leu Arg Leu Lys Pro Leu Thr Gly Glu
145                 150                 155                 160

Gly Thr Ala Gly Gly Gly Gly Gly Arg Arg His Ile Arg Ile Arg
                165                 170                 175

Ser Leu Lys Ile Glu Leu His Ser Arg Ser Gly His Trp Gln Ser Ile
            180                 185                 190

Asp Phe Lys Gln Val Leu His Ser Trp Phe Arg Gln Pro Gln Ser Asn
        195                 200                 205

Trp Gly Ile Glu Ile Asn Ala Phe Asp Pro Ser Gly Thr Asp Leu Ala
    210                 215                 220

Val Thr Ser Leu Gly Pro Gly Ala Glu Gly Leu His Pro Phe Met Glu
225                 230                 235                 240

Leu Arg Val Leu Glu Asn Thr Lys Arg Ser Arg Arg Asn Leu Gly Leu
                245                 250                 255

Asp Cys Asp Glu His Ser Ser Glu Ser Arg Cys Cys Arg Tyr Pro Leu
            260                 265                 270

Thr Val Asp Phe Glu Ala Phe Gly Trp Asp Trp Ile Ile Ala Pro Lys
        275                 280                 285

-continued

```
Arg Tyr Lys Ala Asn Tyr Cys Ser Gly Gln Cys Glu Tyr Met Phe Met
    290                 295                 300

Gln Lys Tyr Pro His Thr His Leu Val Gln Gln Ala Asn Pro Arg Gly
305                 310                 315                 320

Ser Ala Gly Pro Cys Cys Thr Pro Thr Lys Met Ser Pro Ile Asn Met
                325                 330                 335

Leu Tyr Phe Asn Asp Lys Gln Gln Ile Ile Tyr Gly Lys Ile Pro Gly
            340                 345                 350

Met Val Val Asp Arg Cys Gly Cys Ser
        355                 360
```